(12) United States Patent
Ishihara

(10) Patent No.: US 8,295,917 B2
(45) Date of Patent: Oct. 23, 2012

(54) FLUORESCENCE ENDOSCOPE AND FLUOROMETRY METHOD

(75) Inventor: Yasushige Ishihara, Tokyo (JP)

(73) Assignee: Olympus Corporation, Tokyo (JP)

(*) Notice: Subject to any disclaimer, the term of this patent is extended or adjusted under 35 U.S.C. 154(b) by 562 days.

(21) Appl. No.: 12/520,932

(22) PCT Filed: Dec. 25, 2007

(86) PCT No.: PCT/JP2007/074835
§ 371 (c)(1),
(2), (4) Date: Jun. 23, 2009

(87) PCT Pub. No.: WO2008/078742
PCT Pub. Date: Jul. 3, 2008

(65) Prior Publication Data
US 2010/0049058 A1    Feb. 25, 2010

(30) Foreign Application Priority Data

Dec. 25, 2006  (JP) ................................. 2006-347975

(51) Int. Cl.
*A61B 1/06*    (2006.01)
*A61B 6/00*    (2006.01)
*G06K 9/00*    (2006.01)

(52) U.S. Cl. .................... 600/477; 600/160; 382/128

(58) Field of Classification Search .............. 600/160, 600/109, 178–182, 473, 477, 664, 665, 659; 382/128, 191
See application file for complete search history.

(56) References Cited

U.S. PATENT DOCUMENTS

| | | | |
|---|---|---|---|
| 5,749,830 A * | 5/1998 | Kaneko et al. ............... | 600/160 |
| 6,276,798 B1 * | 8/2001 | Gil et al. ...................... | 351/206 |
| 6,323,880 B1 * | 11/2001 | Yamada ........................ | 345/690 |
| 6,364,829 B1 * | 4/2002 | Fulghum ....................... | 600/160 |
| 6,419,361 B2 * | 7/2002 | Cabib et al. .................. | 351/221 |
| 6,521,394 B1 * | 2/2003 | Whitesides et al. .......... | 430/350 |
| 7,328,059 B2 * | 2/2008 | Sevick-Muraca et al. .... | 600/473 |
| 2002/0168096 A1 * | 11/2002 | Hakamata et al. ............ | 382/132 |

FOREIGN PATENT DOCUMENTS

| | | |
|---|---|---|
| JP | 2001-137173 | 5/2001 |
| JP | 2003-164414 | 6/2003 |
| JP | 2003-290130 | 10/2003 |
| JP | 2004-024392 | 1/2004 |
| JP | 2006-191989 | 7/2006 |

* cited by examiner

*Primary Examiner* — Michael Rozanski
*Assistant Examiner* — Lawrence Laryea
(74) *Attorney, Agent, or Firm* — Scully, Scott, Murphy & Presser, P.C.

(57) ABSTRACT

A fluorescence endoscope and a fluorometry method that allow distinguishing between normal and affected areas in a simple manner by reducing the effect of the distance from a subject. A light source that emits light for irradiation of a subject, fluorescence image-acquiring section for acquiring an image of fluorescence contained in return light originating from the subject, fluorescence-image generating section for generating fluorescence image data based on fluorescence-related data acquired by the fluorescence image-acquiring section, region-of-concern defining section for defining a region of concern with a higher fluorescence intensity than a surrounding region based on the fluorescence image data, neighboring-region defining section for defining a neighboring region near the region of concern, and image-operation section for generating corrected image data based on the ratio of a grayscale level related to fluorescence intensity in the region of concern to a grayscale level related to fluorescence intensity in the neighboring region.

13 Claims, 21 Drawing Sheets

FLUORESCENCE ENDOSCOPE AND FLUOROMETRY METHOD

TECHNICAL FIELD

The present invention relates to fluorescence endoscopes and fluorometry methods capable of identifying affected areas based on fluorescence images resulting from excitation light.

BACKGROUND ART

Recently, some techniques have been developed to diagnose the state of a disease, such as cancer, in living tissue using a chemical agent that accumulates in a diseased area such as cancer and that emits fluorescence when irradiated with excitation light. In particular, a technique is known in which a living body is irradiated with excitation light from, for example, a fluorescence endoscope, with the above chemical agent injected into the living body, fluorescence emitted from the chemical accumulated in the diseased area is detected as a two-dimensional image with, for example, the fluorescence endoscope, and the diseased area is diagnosed from the detected fluorescence image.

In such a technique, if the diseased area is located farther away than a normal area, the intensity of the fluorescence emitted from the chemical agent in the diseased area is lower because of the lower intensity per unit area of the excitation light irradiating the chemical agent in the diseased area. For example, there is a case where the excitation light diverges in a conical shape, and the intensity per unit area of the excitation light is approximately inversely proportional to the square of the distance between the distal end of the endoscope and the diseased area.

Various techniques have been proposed that can distinguish between a diseased area and a normal area without being affected by the difference between the distance to the diseased area and the distance to the normal area (see, for example, Patent Documents 1 to 3).

Patent Documents 1 and 2 mentioned above both disclose techniques for distinguishing between a diseased area and a normal area in a subject based on a fluorescence image related to fluorescence emitted from the subject and a reference-light image related to reflected light reflected from the subject upon irradiation with reference light. Specifically, the diseased area and the normal area are distinguished by determining the ratio of the luminance value of a predetermined region in the fluorescence image to that of the corresponding region in the reference-light image to reduce the effect of the distance difference.

In such a technique, reflected light specularly reflected from the surface of the subject can be detected, depending on the relative positional relationship between, for example, the distal end of the endoscope from which the reference light exits and the subject. That is, if reflected light of reference light specularly reflected from the surface of the subject is detected, only the luminance of the region where the specular reflection has occurred is prominent irrespective of the distance from the subject. Consequently, if the ratio of the luminance value of the fluorescence image to the luminance value of the reference light image is determined, the value of the ratio is significantly low only in the region where the specular reflection has occurred.

Patent Document 3 discloses a technique in which fluorescence in two wavelength bands emitted from a subject by irradiation with excitation light is detected, and a diseased area and a normal area in the subject are distinguished based on the ratio of the intensity value of the fluorescence in one wavelength band to the intensity value of the fluorescence in the other wavelength band. In this case, only the fluorescence emitted from the subject is detected, and no light reflected from the surface of the subject is detected, so that the diseased area and the normal area can be distinguished irrespective of whether or not specular reflection has occurred at the surface of the subject.

Patent Document 1:
Japanese Unexamined Patent Application, Publication No. 2001-137173
Patent Document 2:
Japanese Unexamined Patent Application, Publication No. 2003-290130
Patent Document 3:
Japanese Unexamined Patent Application, Publication No. 2004-024932

DISCLOSURE OF INVENTION

In Patent Document 3 above, the endoscope is configured such a plurality of detectors for fluorescence examination provided or a plurality of excitation-light cut filters provided in a switchable manner in order to separately detect fluorescence in two wavelength bands.

The present invention provides a fluorescence endoscope and a fluorometry method capable of acquiring images of normal and affected areas with a reduced effect of the distance from a subject, in a simple configuration, using fluorescence in a single wavelength band.

A first aspect of the present invention provides a fluorescence endoscope including a light source that emits light for irradiation of a subject, fluorescence image-acquiring section for acquiring an image of fluorescence contained in return light originating from the subject, fluorescence-image generating section for generating fluorescence image data based on fluorescence-related data acquired by the fluorescence image-acquiring section, region-of-concern defining section for defining a region of concern with a higher fluorescence intensity than a surrounding region based on the fluorescence image data, neighboring-region defining section for defining a neighboring region near the region of concern, and image-operation section for generating corrected image data based on the ratio of a grayscale level related to fluorescence intensity in the region of concern to a grayscale level related to fluorescence intensity in the neighboring region.

According to the first aspect of the present invention, the region-of-concern defining section defines the region of concern, the neighboring-region defining section defines the vicinity of the region of concern as the neighboring region, and the image-operation section generates the corrected image data based on the ratio of the grayscale levels related to fluorescence intensity in the region of concern and the neighboring region. As a result, the fluorescence endoscope of the present invention can acquire an image of normal and affected areas with a reduced effect of the distance from the subject with a simple configuration using fluorescence in a single wavelength band.

As described above, because a chemical agent that emits fluorescence tends to accumulate in an affected area and fluorescence emitted from the affected area has high intensity, the region-of-concern defining section can define a region that is possibly an affected area as the region of concern by defining a region with high fluorescence intensity as the region of concern based on the fluorescence image data. The neighboring-region defining section can define the neighboring region adjacent to the region of concern, which is defined by the region-of-concern defining section and is possibly an affected area, as a region that is possibly a normal area.

The image-operation section can generate corrected image data with a reduced effect of the distance from the subject based on the ratio of the grayscale level related to fluorescence intensity in the region of concern to the grayscale level related to fluorescence intensity in the neighboring region adjacent to the region of concern. Specifically, the image-operation section can generate corrected image data that allows simultaneous evaluation of grayscale levels related to a plurality of regions of concern that differ in the distance between the light source and the fluorescence image-acquiring section by arithmetically determining the ratios of the grayscale levels related to the regions of concern to the grayscale levels related to the neighboring regions, which have little difference from the regions of concern in the distance between the light source and the fluorescence image-acquiring means. As a result, the image-operation section can generate corrected image data that allows distinguishing between normal and affected areas among the plurality of regions of concern.

The image-operation section can generate corrected image data with a reduced effect of the distance from the subject by determining the ratio of the grayscale levels related to fluorescence intensity in the region of concern and the neighboring region in a single set of fluorescence image data. The fluorescence endoscope of the present invention can therefore acquire an image of normal and affected areas with a reduced effect of the distance from the subject with a simple configuration using fluorescence in a single wavelength band.

Because the light source, the fluorescence image-acquiring section, and the fluorescence-image generating section are provided, the fluorescence endoscope of the present invention can acquire the fluorescence image data.

The light source can emit the light for irradiation of the subject. The fluorescence image-acquiring section can acquire an image of the fluorescence contained in the return light originating from the subject. The fluorescence-image generating section can generate the fluorescence image data based on the fluorescence-related data acquired by the fluorescence image-acquiring section.

In the first aspect of the above invention, preferably, the region-of-concern defining section defines the region of concern based on a comparison between a grayscale level related to fluorescence intensity in the fluorescence image data and a predetermined threshold.

By doing so, for example, the region-of-concern defining section can define a region whose grayscale level related to fluorescence intensity in the fluorescence image data is higher than the predetermined grayscale-related threshold as the region of concern, which is possibly an affected area.

In the first aspect of the above invention, preferably, the region-of-concern defining section defines the region of concern based on the rate of spatial change in grayscale level related to fluorescence intensity in the fluorescence image data.

By doing so, the region-of-concern defining section determines the rate of spatial change in grayscale level related to fluorescence intensity by, for example, determining the rate of change in grayscale level related to fluorescence intensity along a predetermined profile in the fluorescence image data. Because the grayscale level related to fluorescence intensity differs between normal and affected areas, the boundary between the normal and affected areas has a high rate of change in grayscale level related to fluorescence intensity. Accordingly, the region-of-concern defining section can define, as the region of concern, a region whose grayscale level related to fluorescence intensity is high by determining a site where the above rate of change is high.

In the first aspect of the above invention, preferably, the neighboring-region defining section is configured to define, as the neighboring region, a region up to a position separated from the boundary of the region of concern by a predetermined distance.

By doing so, the neighboring-region defining section can define a region surrounding the region of concern and having a thickness equal to the predetermined distance as the neighboring region. Thus, the neighboring-region defining section can always define a region adjacent to the region of concern as the neighboring region.

In the above configuration, preferably, the predetermined distance is defined in a direction crossing the incident plane of the light incident on the subject.

By doing so, because the distance from the position from which the light incident on the subject exits to the surface of the subject varies most in the direction along the incident plane, the effect of the distance to the subject can be reduced by defining the predetermined distance in the direction crossing the incident plane. In particular, the effect of the distance to the subject can be reduced most by defining the predetermined distance in the direction perpendicular to the incident plane.

In the first aspect of the above invention, preferably, the neighboring-region defining section defines, as the neighboring region, a region up to a position separated from a predetermined position in the region of concern by a predetermined distance.

By doing so, because the neighboring-region defining section defines, as the neighboring region, the region from the boundary of the region of concern to the position separated from the predetermined position in the region of concern by the predetermined distance, a region adjacent to the region of concern can be defined as the neighboring region.

Because the neighboring-region defining section defines a region surrounding the region of concern as the neighboring region by defining the position separated from the predetermined position by the predetermined distance as a boundary with a normal area, the neighboring-region defining section can always define a region adjacent to the region of concern as the neighboring region.

The method of defining the boundary between the neighboring region and the normal area based on the distance from the predetermined position in the region of concern allows easier definition than the method of definition based on the distance from the boundary with the region of concern.

In the first aspect of the above invention, preferably, the region-of-concern defining section includes region-of-concern representative-value calculating section for calculating a representative value of the grayscale level related to fluorescence intensity in the region of concern, the neighboring-region defining section includes neighboring-region representative-value calculating section for calculating a representative value of the grayscale level related to fluorescence intensity in the neighboring region, and the image-operation section generates the corrected image data based on the ratio of the representative grayscale level of the region of concern to the representative grayscale level of the neighboring region.

By doing so, the image-operation section generates the corrected image data based on the ratio of the representative grayscale level of the region of concern calculated by the region-of-concern representative-value calculating section to the representative grayscale level of the neighboring region calculated by the neighboring-region representative-value calculating section. The image-operation section can therefore generate corrected image data that allows simultaneous evaluation of representative grayscale values of a plurality of regions of concern that differ in the distance between the light source and the fluorescence image-acquiring section. As a result, the fluorescence endoscope of the present invention can acquire an image that allows distinguishing between normal and affected areas among the plurality of regions of concern.

In the first aspect of the above invention, preferably, image-identifying section for identifying an affected area based on the corrected image data, image-combining section for combining the corrected image data and the affected area identified by the image-identifying section to generate combined image data, and image-displaying section for displaying the combined image data are provided.

By doing so, the combined image data is generated by the image-combining section based on the corrected image data and the affected area identified by the image-identifying section and is displayed on the image-displaying section. As a result, the fluorescence endoscope of the present invention can acquire an image of normal and affected areas with a reduced effect of the distance from the subject with a simple configuration using fluorescence in a single wavelength band.

Because the image-identifying section identifies an affected area based on corrected image data, generated by the image-operation section, with a reduced effect of the distance from the subject, the image-identifying section can distinguish between normal and affected areas while reducing the effect of the distance from the subject. The image-combining section can combine the corrected image data and the affected area identified by the image-identifying section to generate combined image data in which the affected area is distinguished from the normal area.

Because the image-displaying section displays a combined image based on the combined image data, the operator of the endoscope of the present invention can view a combined image displayed on the image-displaying section in which the affected area is distinguished from the normal area.

In the first aspect of the above invention, preferably, image-identifying section for identifying an affected area based on the corrected image data, image-combining section for combining the corrected image data and the affected area identified by the image-identifying section to generate combined image data, and image-displaying section for displaying the combined image data are provided; and the image-identifying section identifies the affected area based on a comparison between the ratio of the representative grayscale level of the region of concern to the representative grayscale level of the neighboring region and a predetermined threshold.

By doing so, the image-identifying section can identify, as the affected area, a region where the ratio of the representative grayscale value of the region of concern to the representative grayscale value of the neighboring region is higher than the predetermined threshold. Thus, by identifying the affected area with the ratio of the representative grayscale value of the region of concern to the representative grayscale value of the neighboring region, the image-identifying section can distinguish between normal and affected areas while reducing the effect of the distance from the subject.

In the first aspect of the above invention, preferably, image-identifying section for identifying an affected area based on the corrected image data, image-combining section for combining the corrected image data and the affected area identified by the image-identifying section to generate combined image data, and image-displaying section for displaying the combined image data are provided; the region-of-concern representative-value calculating section calculates the representative grayscale value of the region of concern based on a grayscale level related to the fluorescence intensity of fluorescence emitted from a fluorescent dye introduced into the subject; and the neighboring-region representative-value calculating section calculates the representative grayscale value of the neighboring region based on a grayscale level related to the intensity of autofluorescence emitted from the subject.

By doing so, the representative grayscale value of the region of concern is calculated by the region-of-concern representative-value calculating section based on the grayscale level related to the fluorescence intensity of the fluorescence emitted from the fluorescent dye, and the representative grayscale value of the neighboring region is calculated by the neighboring-region representative-value calculating section based on the grayscale level related to the fluorescence intensity of the autofluorescence. That is, with the representative grayscale value of the region of concern and the representative grayscale value of the neighboring region, an image of normal and affected areas with a reduced effect of the distance from the subject can be acquired.

The representative grayscale value of the region of concern is calculated based on the grayscale level related to the fluorescence intensity of the fluorescence emitted from the fluorescent dye. The region-of-concern representative-value calculating section can therefore define the representative grayscale value based on the grayscale level related to the fluorescence intensity of the fluorescence emitted from the fluorescent dye, which is related to an affected area, as the representative value of the region of concern, which is possibly an affected area, in which the fluorescent dye tends to accumulate. The representative grayscale value of the neighboring region is calculated based on the grayscale level related to the fluorescence intensity of the autofluorescence. The neighboring-region representative-value calculating section can therefore define the representative grayscale value based on the grayscale level related to the fluorescence intensity of the autofluorescence as the representative value of the neighboring region, which is possibly a normal area, in which the fluorescent dye does not tend to accumulate.

Thus, the fluorescence endoscope of the present invention can distinguish between normal and affected areas while reducing the effect of the distance from the subject.

In the first aspect of the above invention, preferably, reflected-light image-acquiring section for acquiring an image of reflected light contained in the return light, reflected-light-image generating section for generating reflected-light image data based on reflected-light-related data acquired by the reflected-light image-acquiring section, and image-combining section for combining the reflected-light image data and the corrected image data are provided.

By doing so, the image of the reflected light contained in the return light is acquired by the reflected-light image-acquiring section, and the reflected-light image data is generated by the reflected-light-image generating section. The reflected-light image data is combined with the corrected image data by the image-combining section. As a result, the fluorescence endoscope of the present invention can combine reflected-light image data related to reflected light other than fluorescence with fluorescence image data in which an affected area can be easily distinguished from a normal area.

In the first aspect of the above invention, preferably, an insertion portion insertable into a body cavity of the subject and light-conveying section for guiding the light emitted from the light source through the insertion portion to a distal end of the insertion portion and causing the light to exit toward the subject are provided.

By doing so, because the insertion portion for insertion into the body cavity of the subject and the light-conveying section for causing the light to exit from the distal end of the insertion portion toward the subject are provided, an affected area can be distinguished from a normal area in the body cavity of the subject.

The light-conveying section can guide the light emitted from the light source to the distal end of the insertion portion and cause the light to exit from the distal end of the insertion portion inserted into the body cavity toward the subject. Thus, fluorescence can be emitted from normal and affected areas present in the body cavity of the subject, so that the affected area can be distinguished from the normal area in the body cavity of the subject based on the fluorescence intensity of the fluorescence.

A second aspect of the present invention provides a fluorometry method including a fluorescence-image acquiring step of emitting light toward a subject and acquiring fluorescence image data related to fluorescence contained in return light from the subject, a region-of-concern defining step of defining a region of concern with a higher fluorescence intensity than a surrounding region based on the fluorescence image data, a neighboring-region defining step of defining a neighboring region near the region of concern, an operation step of generating corrected image data based on the ratio of a grayscale level related to fluorescence intensity in the region of concern to a grayscale level related to fluorescence intensity in the neighboring region, and an identification step of identifying an affected area based on the ratio of the grayscale level related to fluorescence intensity in the region of concern to the grayscale level related to fluorescence intensity in the neighboring region in the corrected image data and a predetermined threshold.

According to the second aspect of the present invention, the fluorescence image data contained in the return light is acquired in the fluorescence-image acquiring step, the region of concern is defined in the region-of-concern defining step based on the fluorescence image data, and the neighboring region is defined in the neighboring-region defining step. The corrected image data is generated in the operation step based on the ratio of the grayscale levels related to fluorescence intensity in the region of concern and the neighboring region, and the affected area is identified in the identification step based on the ratio of the grayscale levels related to fluorescence intensity in the region of concern and the neighboring region in the corrected image data. As a result, the fluorometry method of the present invention can acquire an image of normal and affected areas with a reduced effect of the distance from the subject with a simple configuration using fluorescence in a single wavelength band.

In the fluorescence-image acquiring step, the light is emitted toward the subject, and the fluorescence image data related to the fluorescence contained in the return light from the subject is acquired.

In the region-of-concern defining step, the region of concern, which is possibly an affected area, is defined based on the acquired fluorescence image data. As described above, because a chemical agent that emits fluorescence tends to accumulate in an affected area and fluorescence emitted from the affected area has high intensity, a region whose fluorescence intensity is higher than the surrounding region and which is possibly an affected area is defined as the region of concern in the region-of-concern defining step. In the neighboring-region defining step, the neighboring region, which is possibly a normal area and is adjacent to the region that is possibly an affected area, is defined.

In the operation step, corrected image data with a reduced effect of the distance from the subject is generated based on the ratio of the grayscale level related to fluorescence intensity in the region of concern defined as described above to the grayscale level related to fluorescence intensity in the neighboring region adjacent to the region of concern.

Because corrected image data with a reduced effect of the distance from the subject is generated in the operation step based on the ratio of the grayscale levels related to fluorescence intensity in the region of concern and the neighboring region in a single set of fluorescence image data, the fluorometry method of the present invention can distinguish between normal and affected areas with a reduced effect of the distance from the subject with a simple configuration using fluorescence in a single wavelength band, as in the techniques disclosed in Patent Documents 1 and 2 mentioned above.

Because the affected area can be identified in the identification step based on corrected image data, generated by the operation step, with a reduced effect of the distance from the subject, an affected area can be distinguished from a normal area while reducing the effect of the distance from the subject. In the identification step, for example, the region of concern can be identified as an affected area if the value of the ratio of the grayscale level related to the region of concern to the grayscale level related to the neighboring region exceeds the predetermined threshold.

The fluorescence endoscope according to the first aspect of the present invention and the fluorometry method according to the second aspect provide the advantage of acquiring an image of normal and affected areas with a reduced effect of the distance from a subject, in a simple configuration, without the use of a reference-light image in addition to a fluorescence image.

Figure 1:
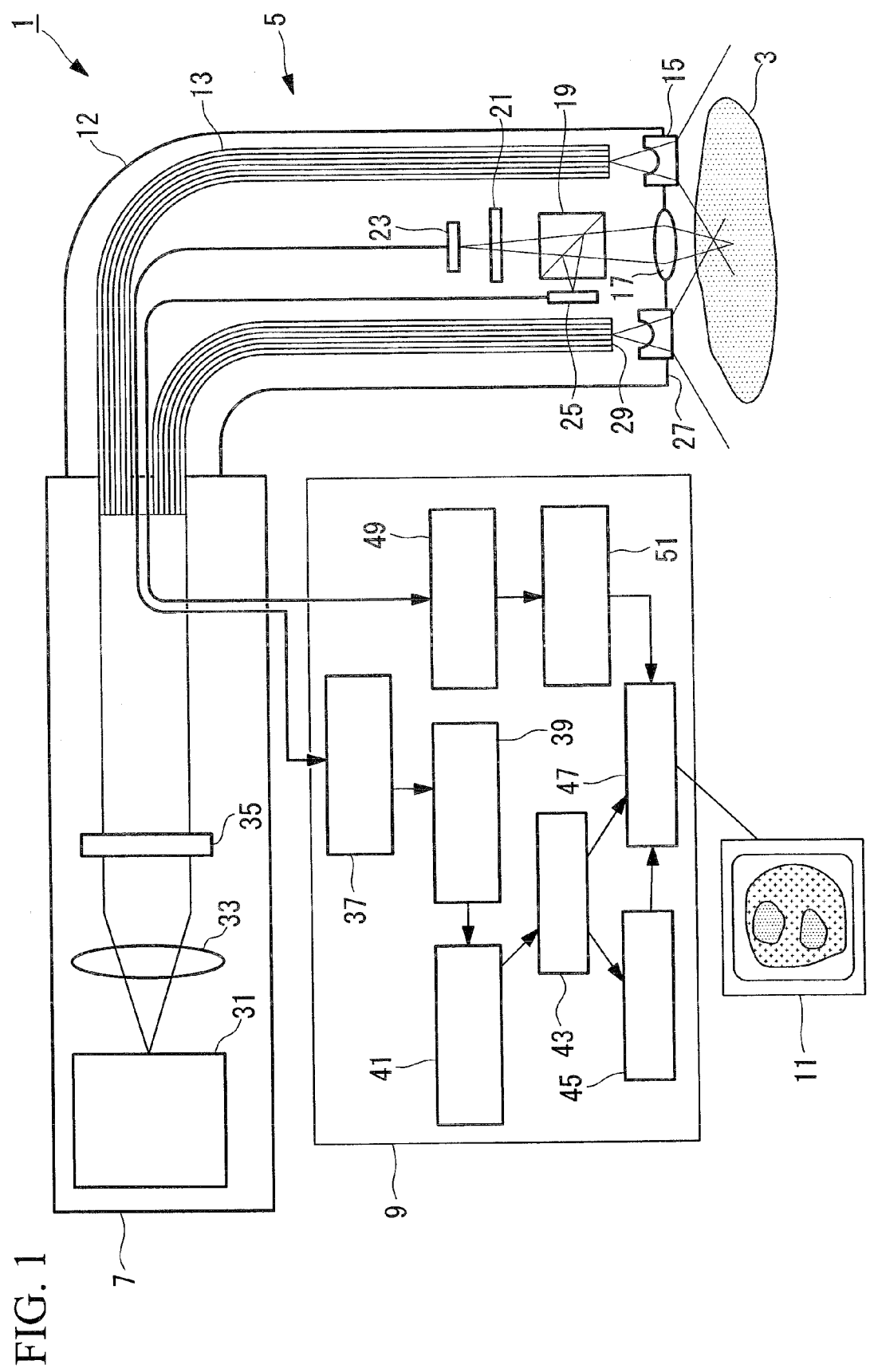
FIG. 1 is a schematic diagram illustrating the configuration of a fluorescence endoscope according to a first embodiment of the present invention.

EXPLANATION OF REFERENCE SIGNS 1, 101, 201, 301: fluorescence endoscope
3: subject
5, 205: insertion portion
7: light source unit (light source)
11: monitor (image-displaying section)
13: light guide (light-conveying section)
23: fluorescence image-acquiring section
25: reflected-light image-acquiring section
37: fluorescence-image generating section
39, 339: region-of-concern defining section (region-of-concern defining section, region-of-concern representative-value calculating section)
41: neighboring-region defining section (neighboring-region defining section, neighboring-region representative-value calculating section)
43: image-operation section
45: image-identifying section
47, 247: image-combining section
49, 249: reflected-light-image generating section
439: region-defining section (region-of-concern defining section, neighboring-region defining section)
CR1, CR2, CR3, CR4, CR11, CR12, CR31, CR32: region of concern
NR1, NR2, NR31, NR32: neighboring region

BEST MODE FOR CARRYING OUT THE INVENTION

First Embodiment

A fluorescence endoscope according to a first embodiment of the present invention will now be described with reference to FIGS. 1 to 18.

FIG. 1 is a schematic diagram illustrating the configuration of the fluorescence endoscope according to this embodiment.

As shown in FIG. 1, a fluorescence endoscope 1 includes an insertion portion 5 for insertion into the body cavity of a subject 3, a light source unit (light source) 7, an image-generating unit 9, and a monitor (image-displaying section) 11.

The insertion portion 5 is inserted into the body cavity of the subject 3 and is formed in a substantially cylindrical shape.

The insertion portion 5 includes an outer tube 12, a light guide (light-conveying section) 13, an illumination lens 15, an image-acquisition lens 17, a dichroic prism 19, an excitation-light cut filter 21, a fluorescence image-acquiring section 23, and a reflected-light image-acquiring section 25.

The outer tube 12 is a cylindrical member constituting the peripheral surface of the insertion portion 5 and is a tube formed of a flexible material. The light guide 13 and so on are disposed inside the outer tube 12.

The light guide 13 guides excitation light and illumination light emitted from the light source unit 7 to a distal end surface 27 of the insertion portion 5 and causes them to exit toward the subject 3.

The light guide 13 is constituted of a plurality of fiber bundles that guide light. The light guide 13 is formed in a substantially cylindrical shape extending along substantially the entire length of the insertion portion 5. Disposed inside the light guide 13 are the dichroic prism 19, the excitation-light cut filter 21, the fluorescence image-acquiring section 23, the reflected-light image-acquiring section 25, and so on.

The illumination lens 15 is a lens that spreads the excitation light and the illumination light exiting the light guide 13 toward the entire examination region of the subject 3.

The illumination lens 15 is disposed on the distal end surface 27 of the insertion portion 5 at a position opposite a light-exiting end surface 29 of the light guide 13. The illumination lens 15 is formed in the shape of an annular plate and is formed in the shape of a planoconcave lens.

The image-acquisition lens 17 is a lens that forms images of return light from the subject 3 on the fluorescence image-acquiring section 23 and the reflected-light image-acquiring section 25.

The image-acquisition lens 17 is disposed on the distal end surface 27 of the insertion portion 5 in a region inside the illumination lens 15. Return light herein refers to light propagating from the subject 3 toward the insertion portion 5. The return light contains, for example, fluorescence emitted from a fluorescent dye (chemical agent) introduced into the subject 3; autofluorescence emitted from the subject 3 itself; and reflected light, or illumination light, and excitation light reflected from the surface of the subject 3.

The dichroic prism 19 reflects the reflected light contained in the return light toward the reflected-light image-acquiring section 25 and transmits the fluorescence, the excitation light, and so on contained in the return light toward the fluorescence image-acquiring section 23.

The dichroic prism 19 is disposed inside the light guide 13 near the distal end surface 27 of the insertion portion 5 at a position opposite the image-acquisition lens 17. The reflective surface of the dichroic prism 19 is inclined at an angle of about 45° with respect to the optical axis of the image-acquisition lens 17. The reflective surface reflects only the reflected light contained in the return light entering the dichroic prism 19 and transmits other light. The reflected light reflected by the dichroic prism 19 is the illumination light (white light) reflected from the surface of the subject 3. The dichroic prism 19 used can be a known one and is not specifically limited.

The excitation-light cut filter 21 allows only the fluorescence contained in the light passing through the dichroic prism 19 to enter the fluorescence image-acquiring section 23.

The excitation-light cut filter 21 is disposed on the optical axis of the image-acquisition lens 17 between the dichroic prism 19 and the fluorescence image-acquiring section 23. The fluorescence passing through the excitation-light cut filter 21 contains the fluorescence emitted from the fluorescent dye described above and the autofluorescence emitted from the subject 3 itself. The excitation-light cut filter 21 used can be a known cut filter and is not specifically limited.

The fluorescence image-acquiring section 23 acquires an image of the fluorescence emitted from the subject 3.

The fluorescence image-acquiring section 23 is disposed on the optical axis of the image-acquisition lens 17 at a position opposite the excitation-light cut filter 21. Fluorescence-related data output from the fluorescence image-acquiring section 23 is input to a fluorescence-image generating section 37, described later. The fluorescence image-acquiring section 23 used can be, for example, a planar arrangement of known image-acquisition devices, such as charge-coupled devices (CCD) or complementary metal oxide semiconductor (CMOS) devices, and is not specifically limited.

The fluorescence subjected to the image acquisition by the fluorescence image-acquiring section 23 contains the fluorescence emitted from the fluorescent dye and the autofluorescence emitted from the subject 3 itself.

The reflected-light image-acquiring section 25 acquires an image of the reflected light reflected from the surface of the subject 3.

The reflected-light image-acquiring section 25 is disposed at a position where the reflected light reflected by the dichroic prism 19 is incident. Reflected-light-related data output from the reflected-light image-acquiring section 25 is input to a reflected-light-image generating section 49, described later.

The reflected-light image-acquiring section 25 used can be, for example, a planar arrangement of known image-acquisition devices, such as CCD or CMOS devices, and is not specifically limited.

The light source unit 7 emits excitation light and illumination light for irradiation of the subject 3. The light source unit 7 includes a white light source 31, a light source lens 33, and an optical filter 35.

The white light source 31 emits light including excitation light for excitation of the fluorescent dye and the subject 3 itself and white light for illumination of the subject 3.

The light source lens 33 is a lens that converts the light emitted from the white light source 31 into substantially collimated light to cause it to enter the light guide 13.

The optical filter 35 is a filter that transmits only the excitation light and the illumination light in the light emitted from the white light source 31. The optical filter 35 is disposed between the light source lens 33 and the light guide 13.

The image-generating unit 9 generates image data from which an image is displayed on the monitor 11, based on the fluorescence-related data acquired by the fluorescence image-acquiring section 23 and the reflected-light-related data acquired by the reflected-light image-acquiring section 25.

The image-generating unit 9 includes the fluorescence-image generating section 37, a region-of-concern defining section (region-of-concern defining section, region-of-concern representative-value calculating section) 39, a neighboring-region defining section (neighboring-region defining section, neighboring-region representative-value calculating section) 41, an image-operation section 43, an image-identifying section 45, an image-combining section 47, the reflected-light-image generating section 49, and an examination-distance determining section 51.

The fluorescence-image generating section 37 generates fluorescence image data based on the fluorescence-related data acquired by the fluorescence image-acquiring section 23. The fluorescence-related data is input from the fluorescence image-acquiring section 23 to the fluorescence-image generating section 37. The generated fluorescence image data is output from the fluorescence-image generating section 37 to the region-of-concern defining section 39.

The region-of-concern defining section 39 defines a region of concern based on the fluorescence image data. The fluorescence image data is input from the fluorescence-image generating section 37 to the region-of-concern defining section 39. Data related to the region of concern and the fluorescence image data are output from the region-of-concern defining section 39 to the neighboring-region defining section 41.

The neighboring-region defining section 41 defines a neighboring region adjacent to the region of concern. The data related to the region of concern and the fluorescence image data are input from the region-of-concern defining section 39 to the neighboring-region defining section 41. Data related to the neighboring region, the data related to the region of concern, and the fluorescence image data are output from the neighboring-region defining section 41 to the image-operation section 43.

The image-operation section 43 generates corrected image data based on the ratio of a grayscale level related to fluorescence intensity in the region of concern to a grayscale level related to fluorescence intensity in the neighboring region. The data related to the neighboring region, the data related to the region of concern, and the fluorescence image data are input from the neighboring-region defining section 41 to the image-operation section 43. The corrected image data is output from the image-operation section 43 to the image-identifying section 45 and the image-combining section 47.

The image-identifying section 45 identifies an affected area based on the corrected image data. The corrected image data is input from the image-operation section 43 to the image-identifying section 45. Data related to the affected area is output from the image-identifying section 45 to the image-combining section 47.

The reflected-light-image generating section 49 generates reflected-light image data based on the reflected-light-related data acquired by the reflected-light image-acquiring section 25. The reflected-light-related data is input from the reflected-light image-acquiring section 25 to the reflected-light-image generating section 49. The reflected-light image data is output from the reflected-light-image generating section 49 to the examination-distance determining section 51.

The examination-distance determining section 51 determines whether the examination distance falls within an assumed range based on the reflected-light image data. The reflected-light image data is input from the reflected-light-image generating section 49 to the examination-distance determining section 51. The reflected-light image data and data related to the examination distance are output from the examination-distance determining section 51 to the image-combining section 47.

The image-combining section 47 combines the corrected image data, the identified affected area, and the reflected-light image data to generate combined image data. The corrected image data is input from the image-operation section 43 to the image-combining section 47, the data related to the affected area is input from the image-identifying section 45 to the image-combining section 47, and the reflected-light image data and the data related to the examination distance are input from the examination-distance determining section 51 to the image-combining section 47. The combined image data is output from the image-combining section 47 to the monitor 11.

The monitor 11 displays the combined image data generated by the image-generating unit 9 as an image to, for example, the operator of the fluorescence endoscope 1.

Next, examination of the subject 3 and distinguishing between normal and affected areas with the fluorescence endoscope 1 having the above configuration will be described.

Figure 2:
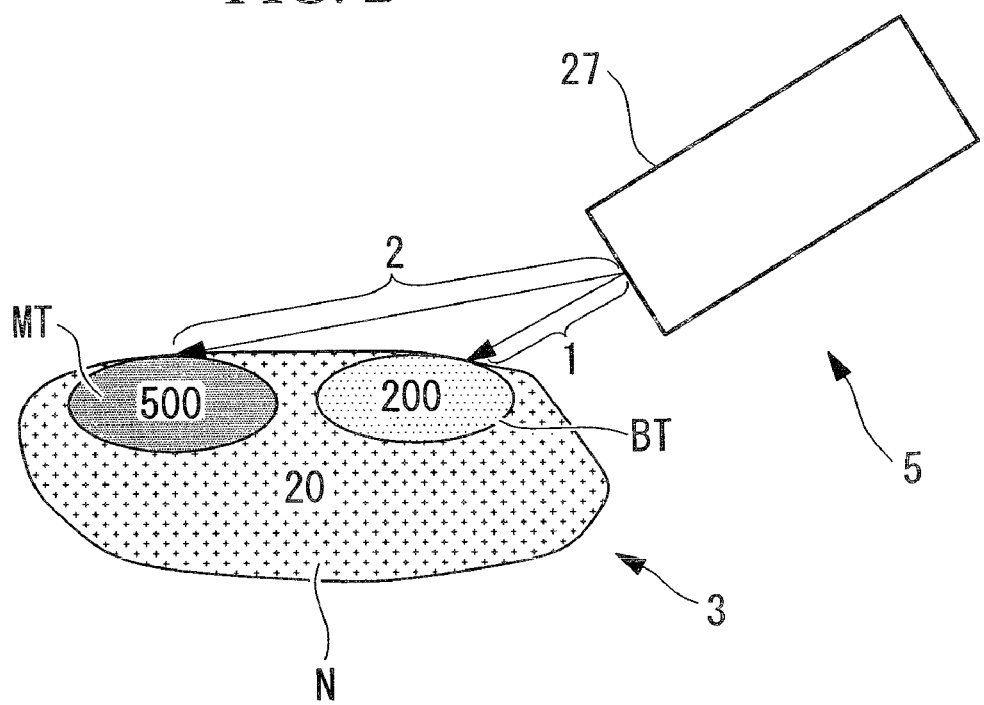
FIG. 2 is a schematic diagram illustrating the relative positional relationship between a subject and an insertion portion.

FIG. 2 is a schematic diagram illustrating the relative positional relationship between the subject 3 and the insertion portion 5.

Described herein is a method for examining a subject 3 having normal tissue N and a benign tumor BT, which are normal areas, and a cancer MT, which is an affected area, with the fluorescence endoscope 1, as shown in FIG. 2, to distinguish between the normal tissue N, the benign tumor BT, and the cancer MT. The insertion portion 5 examines the subject 3 from above and at an inclination relative to the subject 3. Specifically, with the distance from the distal end surface 27 of the subject 3 to the benign tumor BT serving as a reference (=1), the insertion portion 5 and the subject 3 are located so that the distance from the distal end surface 27 to the cancer MT is twice as large (=2). The luminances of fluorescence emitted from the normal tissue N, benign tumor BT, and cancer MT of the subject 3 are 20, 200, and 500, respectively. These values are those in the case where the conditions of excitation light for irradiation of the normal tissue N, benign tumor BT, and cancer MT of the subject 3 and so on are identical.

The case where the luminances of the fluorescence from the normal tissue N, the benign tumor BT, and the cancer MT are 20, 200, and 500, respectively, will be described herein.

First, a fluorescent dye (chemical agent) that emits fluorescence upon irradiation with excitation light is administered to the subject 3. This fluorescent dye has a property to accumulate in an affected area, such as the cancer MT, in the subject 3. Examination with the fluorescence endoscope 1 is carried out after the fluorescent dye is administered to the subject 3 and a period of time required for the chemical agent to spread sufficiently throughout the subject 3 has passed.

For examination with the fluorescence endoscope 1, as shown in FIG. 1, the light source unit 7 first emits excitation light and illumination light.

That is, the white light source 31 emits light containing at least excitation light and illumination light. The light source lens 33 converts the light emitted from the white light source 31 into substantially collimated light to cause it to exit toward the light guide 13. The light passing through the light source lens 33 enters the optical filter 35. The optical filter 35 transmits only the excitation light and the illumination light in the incident light and blocks light with other wavelengths. The excitation light and the illumination light passing through the optical filter 35 exit the light source unit 7.

The excitation light and the illumination light emitted from the light source unit 7 irradiate the subject 3.

That is, the excitation light and the illumination light emitted from the light source unit 7 enter the light guide 13 in the insertion portion 5. The light guide 13 guides the incident excitation light and illumination light to the distal end surface 27 of the insertion portion 5 and causes the excitation light and the illumination light to exit toward the subject 3. The excitation light and the illumination light exiting the light guide 13 irradiate the subject 3 through the illumination lens 15. The illumination lens 15 spreads the light exiting the light guide 13 to irradiate the entire examination region of the subject 3 with the excitation light and the illumination light.

Images of return light from the subject 3 irradiated with the excitation light and the illumination light are acquired by the fluorescence image-acquiring section 23 and the reflected-light image-acquiring section 25.

That is, the return light from the subject 3 enters the insertion portion 5 through the image-acquisition lens 17. The image-acquisition lens 17 forms images of the subject 3 with the incident return light on the light-receiving surfaces of the fluorescence image-acquiring section 23 and the reflected-light image-acquiring section 25. The return light passing through the image-acquisition lens 17 enters the dichroic prism 19. The dichroic prism 19 reflects only reflected light contained in the return light toward the reflected-light image-acquiring section 25. Accordingly, a reflected-light image of the subject 3 is formed on the light-receiving surface of the reflected-light image-acquiring section 25. The remaining light passes through the dichroic prism 19 and enters the excitation-light cut filter 21. The excitation-light cut filter 21 transmits only fluorescence contained in the remaining light and blocks light with other wavelengths, including the excitation light. The fluorescence passing through the excitation-light cut filter 21 enters the fluorescence image-acquiring section 23. Accordingly, a fluorescence image of the subject 3 is formed on the light-receiving surface of the fluorescence image-acquiring section 23.

The fluorescence image-acquiring section 23 and the reflected-light image-acquiring section 25 acquire the formed fluorescence image of the subject 3 and the formed reflected-light image of the subject 3, respectively, and output fluorescence-related data and reflected-light-related data (fluorescence-image acquiring step).

The fluorescence-related data is a set of data output from the individual image-acquisition devices in the fluorescence image-acquiring section 23 depending on the intensity of the fluorescence received. The reflected-light-related data is a set of data output from the individual image-acquisition devices in the reflected-light image-acquiring section 25 depending on the intensity of the reflected light received.

Figure 3:
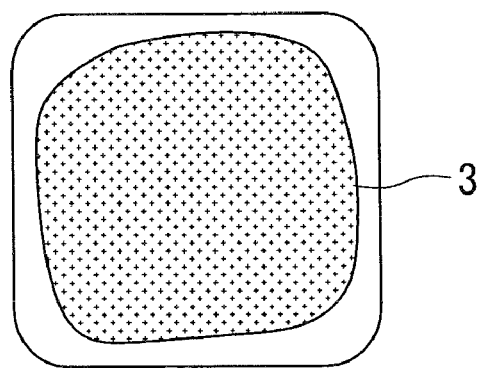
FIG. 3 is a diagram showing an image related to fluorescence image data generated by a fluorescence-image generating section in FIG. 1.

FIG. 3 is a diagram showing an image related to fluorescence image data generated by the fluorescence-image generating section 37 in FIG. 1.

The fluorescence-related data output from the fluorescence image-acquiring section 23 and the reflected-light-related data output from the reflected-light image-acquiring section 25 are input to the image-generating unit 9 and are converted into combined image data to be displayed on the monitor 11.

That is, the fluorescence-related data is input to the fluorescence-image generating section 37 of the image-generating unit 9. Based on the fluorescence-related data, the fluorescence-image generating section 37 generates fluorescence image data related to a fluorescence image as shown in FIG. 3. Fluorescence image data herein refers to a set of data related to a plurality of pixels, constituting a fluorescence image, that correspond to the individual image-acquisition devices of the fluorescence image-acquiring section 23. The data on the individual pixels in the fluorescence image data can be exemplified by data on the positions thereof in the fluorescence image and data on the grayscale levels thereof depending on the fluorescence intensity of fluorescence.

Figure 4:
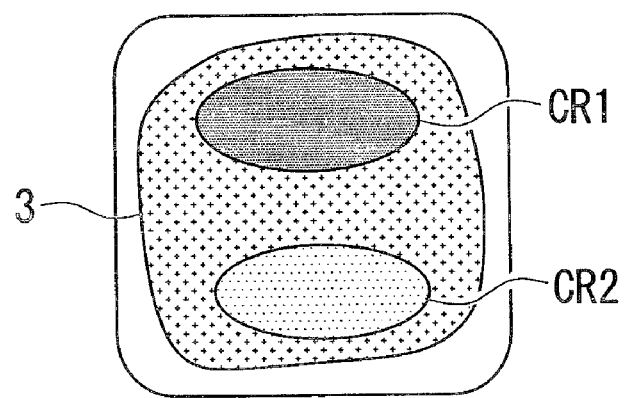
FIG. 4 is a diagram showing regions of concern defined by a region-of-concern defining section in FIG. 1.
Figure 5:
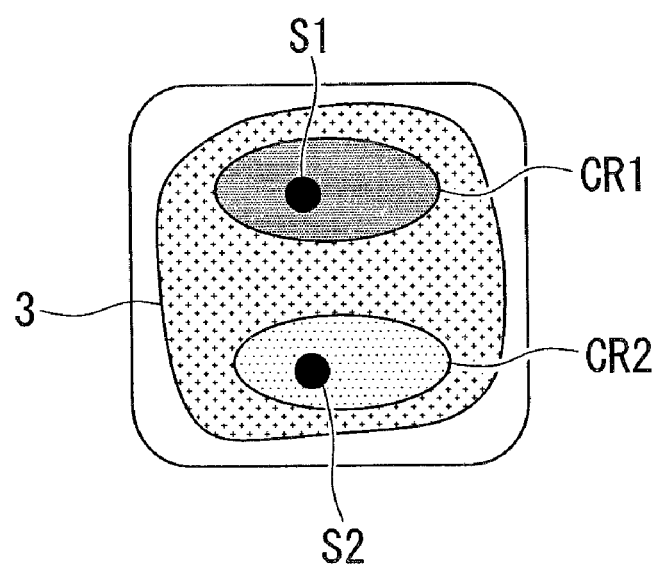
FIG. 5 is a diagram showing extraction of the maximum grayscale levels of the individual regions of concern by the region-of-concern defining section in FIG. 1.

FIG. 4 is a diagram showing regions of concern defined by the region-of-concern defining section 39 in FIG. 1. FIG. 5 is a diagram showing extraction of the maximum grayscale levels of the individual regions of concern by the region-of-concern defining section 39 in FIG. 1.

As shown in FIG. 1, the fluorescence image data generated by the fluorescence-image generating section 37 is input to the region-of-concern defining section 39. The region-of-concern defining section 39 defines regions of concern CR based on the fluorescence image data (region-of-concern defining step).

That is, as shown in FIG. 4, the region-of-concern defining section 39 extracts regions of pixels with grayscale levels equal to or higher than a region-of-concern threshold, described later, as regions of concern CR1 and CR2 from the fluorescence image data. The regions of concern CR1 and CR2 correspond to the cancer MT and the benign tumor BT, respectively. In this embodiment, the case where the region-of-concern threshold is 45 will be described. The value of the region-of-concern threshold is not limited to the above value because it is determined based on various factors, including the type of fluorescent dye used, the wavelength and amount of the excitation light, and the distance from the distal end surface 27 of the insertion portion 5 to the subject 3.

After defining the regions of concern CR1 and CR2, the region-of-concern defining section 39, as shown in FIG. 5, extracts pixels with the maximum grayscale levels in the individual regions of concern CR1 and CR2 as representative pixels S1 and S2, respectively, and acquires data on the positions and grayscale levels of those pixels as representative values.

The region-of-concern threshold used for extraction of the regions of concern CR1 and CR2 will be described herein.

The actual luminances are known values determined by, for example, experiment, that is, the luminances of actually occurring fluorescence. The displayed grayscale levels are the grayscale levels of the corresponding pixels in the fluorescence image data generated by the fluorescence-image generating section 37 when fluorescence is received by the fluorescence image-acquiring section 23. In addition, the displayed grayscale levels are classified into the displayed grayscale levels in the cases where the distance between the subject 3 and the distal end surface 27 is 1 mm, 1.5 mm, and 2 mm. The distance is specified in the range of 1 to 2 mm for the following reasons. If the distance falls below 1 mm, an image of the subject 3 cannot be formed on the light-receiving surface of the fluorescence image-acquiring section 23 because the subject 3 is located closer to the distal end surface 27 than the focal depth of the image-acquisition lens 17. If the distance exceeds 2 mm, the fluorescence emitted from the subject 3 is significantly attenuated, and therefore the fluorescence image-acquiring section 23 cannot acquire a fluorescence image with sufficient brightness.

Hence, the case where the assumed examination distance is 1 to 2 mm will be described herein.

The displayed grayscale levels for the normal tissue N, the benign tumor BT, and the cancer MT vary inversely with the square of the distance.

In the description below, the distance between the endoscope 1 and the cancer MT is assumed to be 2 mm, and the distance between the endoscope 1 and the benign tumor BT is assumed to be 1 mm. Therefore, the grayscale value of the representative pixel S1 of the region of concern CR1, namely, the representative grayscale value thereof, is 125, whereas the grayscale value of the representative pixel S2 of the region of concern CR2, namely, the representative grayscale value thereof, is 200.

Figure 6:
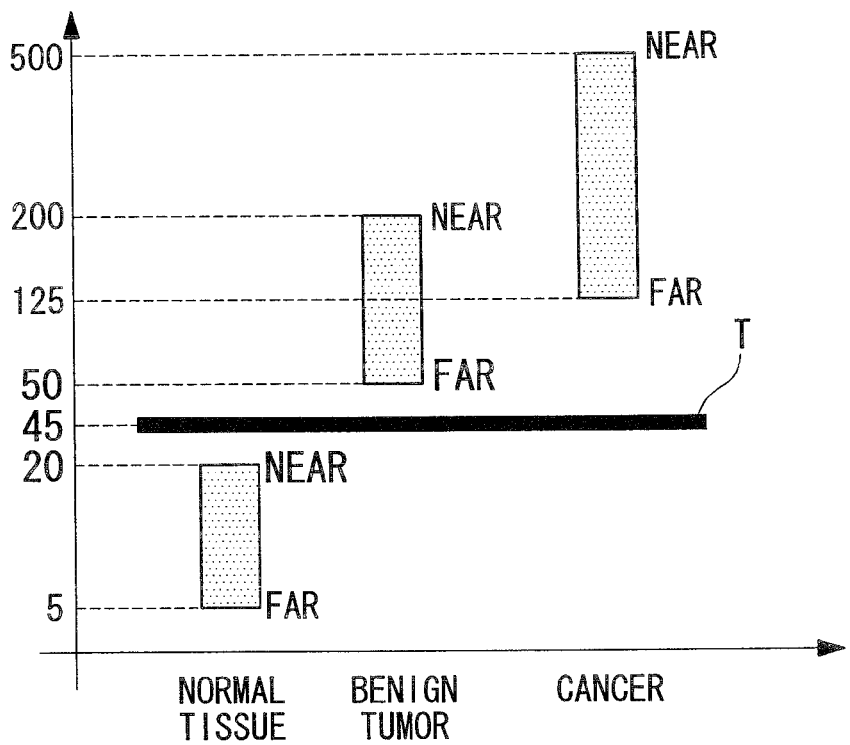
FIG. 6 is a graph showing the ranges of displayed grayscale levels for normal tissue, a benign tumor, and a cancer.

FIG. 6 is a graph showing the ranges of the displayed grayscale levels for the normal tissue, the benign tumor, and the cancer.

The ranges of the displayed grayscale levels for the normal tissue N, the benign tumor BT, and the cancer MT are plotted in the graph shown in FIG. 6. The range of grayscale levels related to the normal tissue N is from 20 to 5. The range of grayscale levels related to the benign tumor BT is from 200 to 50. The range of grayscale levels related to the cancer MT is from 500 to 125. By comparing the ranges of grayscale levels related to the normal tissue N and the benign tumor BT, the maximum value of the grayscale levels related to the normal tissue N is 20, and the minimum value of the grayscale levels related to the benign tumor BT is 50. That is, setting a region-of-concern threshold T between grayscale levels of 20 and 50 allows distinguishing between the region of the normal tissue N and the regions including the benign tumor BT and the cancer MT, which is an affected area, even if the distance between the subject 3 and the distal end surface 27 varies between 1 mm and 2 mm. As a result, the region-of-concern defining section 39 can reliably define a region that is possibly an affected area as a region of concern within the set examination distance.

The ranges of the displayed grayscale levels for the normal tissue N, the benign tumor BT, and the cancer MT shown in Table 1 are plotted in the graph shown in FIG. 6. The range of grayscale levels related to the normal tissue N is from 20 to 5. The range of grayscale levels related to the benign tumor BT is from 200 to 50. The range of grayscale levels related to the cancer MT is from 500 to 125. By comparing the ranges of grayscale levels related to the normal tissue N and the benign tumor BT, the maximum value of the grayscale levels related to the normal tissue N is 20, and the minimum value of the grayscale levels related to the benign tumor BT is 50. That is, setting a region-of-concern threshold T between grayscale levels of 20 and 50 allows distinguishing between the region of the normal tissue N and the regions including the benign tumor BT and the cancer MT, which is an affected area, even if the distance between the subject 3 and the distal end surface 27 varies between 1 mm and 2 mm. As a result, the region-of-concern defining section 39 can reliably define a region that is possibly an affected area as a region of concern within the set examination distance.

Figure 7:
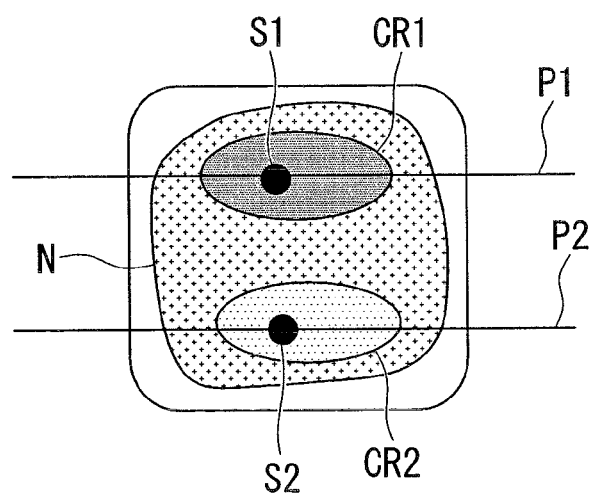
FIG. 7 is a diagram illustrating profile setting by a neighboring-region defining section in FIG. 1.
Figure 8:
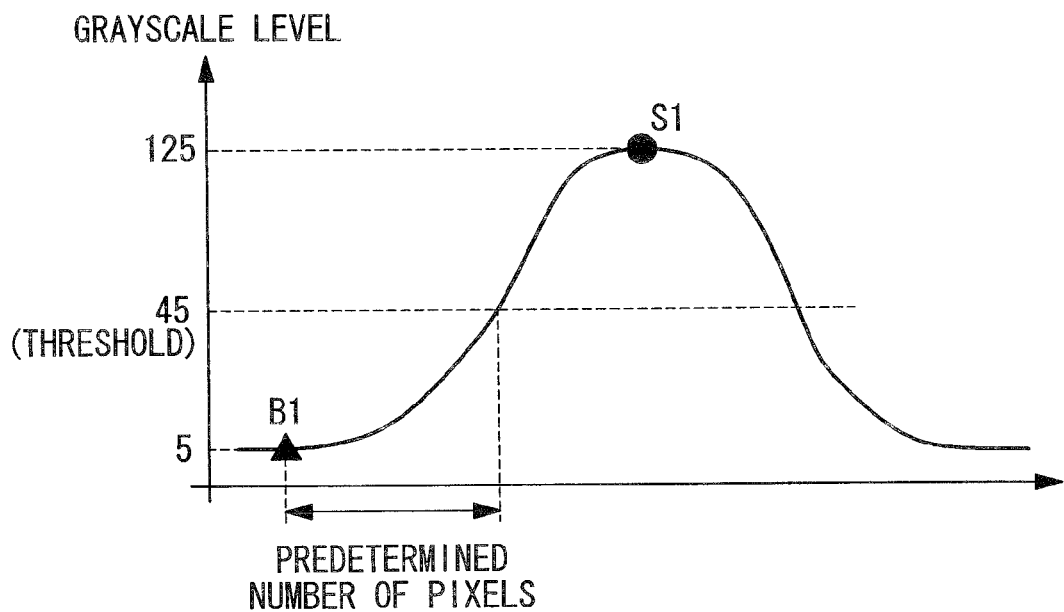
FIG. 8 is a graph showing the distribution of the grayscale levels of individual pixels on a profile P1 in FIG. 7.
Figure 9:
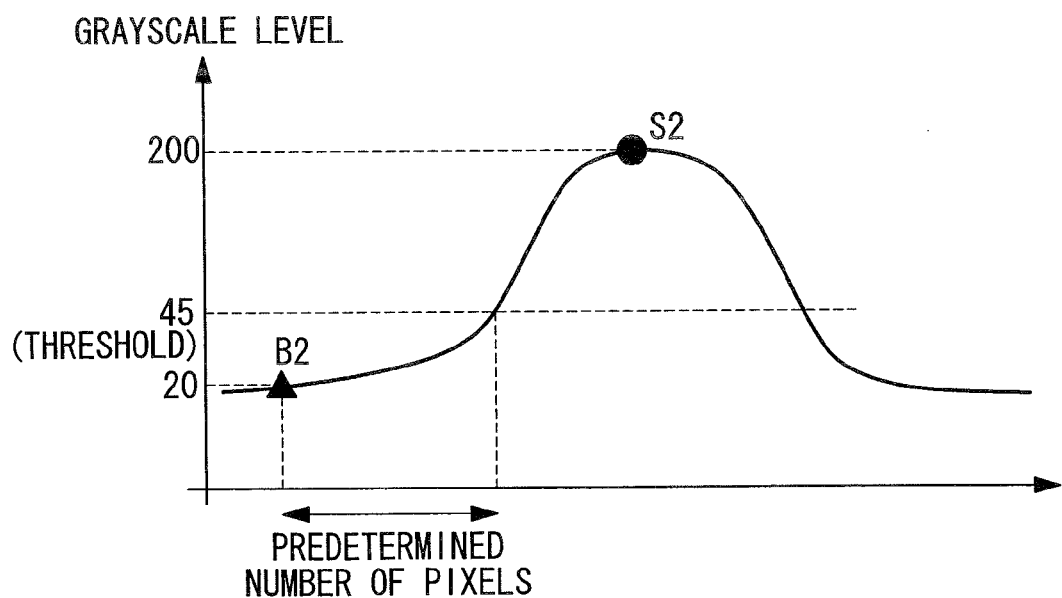
FIG. 9 is a graph showing the distribution of the grayscale levels of individual pixels on a profile P2 in FIG. 7.
Figure 10:
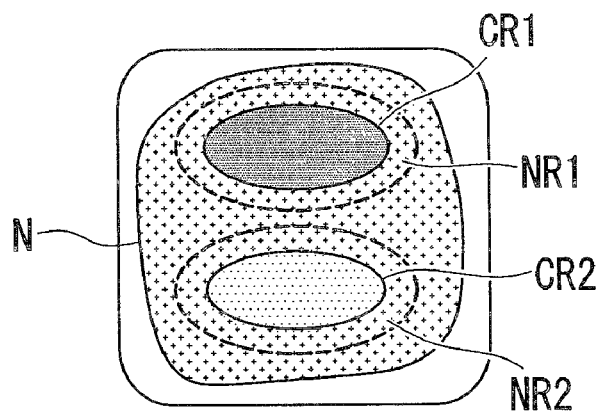
FIG. 10 is a diagram showing the positional relationship between neighboring regions defined by the neighboring-region defining section in FIG. 1 and the regions of concern.

FIG. 7 is a diagram illustrating profile setting by the neighboring-region defining section in FIG. 1. FIG. 8 is a graph showing the distribution of the grayscale levels of the individual pixels on a profile P1 in FIG. 7. FIG. 9 is a graph showing the distribution of the grayscale levels of the individual pixels on a profile P2 in FIG. 7. FIG. 10 is a diagram showing the positional relationship between neighboring regions defined by the neighboring-region defining section in FIG. 1 and the regions of concern.

After the region-of-concern defining section 39 defines the regions of concern CR1 and CR2 and the representative pixels S1 and S2, the fluorescence image data, the data on the regions of concern CR1 and CR2 and the representative pixels S1 and S2, and so on are input to the neighboring-region defining section 41. The neighboring-region defining section 41 defines neighboring regions adjacent to the regions of concern CR1 and CR2 based on the fluorescence image data and so on (neighboring-region defining step).

That is, the neighboring-region defining section 41 sets the profiles P1 and P2 based on the input fluorescence image data and so on. The profiles P1 and P2 are straight lines passing through the representative pixels S1 and S2, and data on the grayscale levels of the individual pixels are extracted along those straight lines.

The grayscale levels of the individual pixels on the profile P1 form a distribution shown in FIG. 8. The grayscale levels of the individual pixels have lower values the farther they are from the representative pixel S1, whose grayscale level (black circle in FIG. 8) is the maximum grayscale level. A region of pixels, including the representative pixel S1, with grayscale values higher than the region-of-concern threshold, namely, 45, indicates the region of concern CR1. The neighboring-region defining section 41 defines as a neighboring region NR1 a region from a pixel with the grayscale level equal to the region-of-concern threshold to a representative pixel B1 (black triangle in FIG. 8) separated along the profile P1 by a predetermined number of pixels. The grayscale value of the representative pixel B1 is a representative grayscale value representing the grayscale levels of the pixels in the neighboring region NR1. In this embodiment, the representative grayscale value of the representative pixel B1 is 5, according to FIG. 8.

On the other hand, the grayscale levels of the individual pixels on the profile P2 form a distribution shown in FIG. 9. The grayscale levels of the individual pixels have lower values the farther they are from the representative pixel S2, whose grayscale level (black circle in FIG. 9) is the maximum grayscale level. A region of pixels, including the representative pixel S2, with grayscale values higher than the region-of-concern threshold, namely, 45, indicates the region of concern CR2. The neighboring-region defining section 41 defines as a neighboring region NR2 a region from a pixel with the grayscale level equal to the region-of-concern threshold to a representative pixel B2 (black triangle in FIG. 9) separated along the profile P2 by a predetermined number of pixels. The grayscale value of the representative pixel B2 is a representative grayscale value representing the grayscale levels of the pixels in the neighboring region NR2. In this embodiment, the representative grayscale value of the representative pixel B2 is 20, according to FIG. 9.

The neighboring regions NR1 and NR2 defined by the neighboring-region defining section 41 as described above are defined so as to surround the peripheries of the regions of concern CR1 and CR2, respectively, as shown in FIG. 10.

Figure 11:
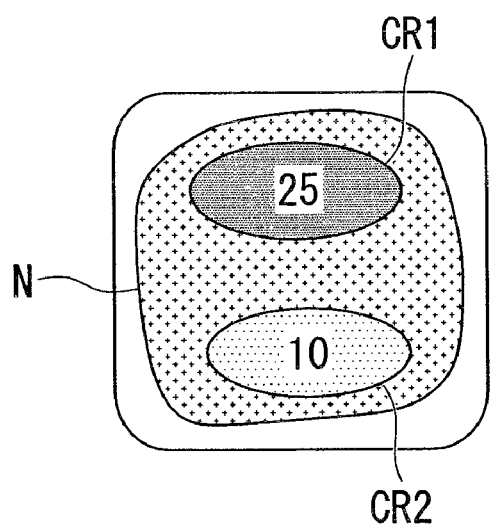
FIG. 11 is a diagram showing an image related to corrected image data generated by an image-operation section in FIG. 1.

FIG. 11 is a diagram showing an image related to corrected image data generated by the image-operation section in FIG. 1.

The data related to the neighboring regions NR1 and NR2 and the data related to the representative pixels B1 and B2 defined by the neighboring-region defining section 41 are input to the image-operation section 43 together with the fluorescence image data, the data related to the regions of concern CR1 and CR2, and the data related to the representative pixels S1 and S2. The image-operation section 43 generates corrected image data based on the input fluorescence image data and so on (operation step).

That is, the image-operation section 43 divides the grayscale level of the representative pixel S1 in the region of concern CR1, namely, 125, by the grayscale level of the representative pixel B1 in the adjacent neighboring region NR1, namely, 5, to yield a value of 25 (the ratio of the grayscale level of the representative pixel S1 to that of the representative pixel B1) as the grayscale level in the region of concern CR1. On the other hand, the image-operation section 43 divides the grayscale level of the representative pixel S2 in the region of concern CR2, namely, 200, by the grayscale level of the representative pixel B2 in the adjacent neighboring region NR2, namely, 20, to yield a value of 10 as the grayscale level in the region of concern CR2. An image related to the corrected image data yielded by the image-operation section 43 is shown in FIG. 11. As shown in FIG. 11, all the pixels belonging to the region of concern CR1 are displayed with a grayscale level of 25, whereas all the pixels belonging to the region of concern CR2 are displayed with a grayscale level of 10.

As shown in FIG. 1, the corrected image data generated by the image-operation section 43 is output to the image-identifying section 45 and the image-combining section 47.

Based on the input corrected image data, the image-identifying section 45 determines whether the individual regions of concern CR1 and CR2 are the benign tumor BT or the cancer MT (identification step).

That is, as shown in FIG. 11, the image-identifying section 45 determines that the regions of concern CR1 and CR2 are the cancer MT if the grayscale values thereof are higher than a distinguishing threshold (identification step) and determines that the regions of concern CR1 and CR2 are the benign tumor BT if the grayscale values thereof are lower than the distinguishing threshold. In this embodiment, the distinguishing threshold is 15; because the grayscale level of the region of concern CR1 is 25, the image-identifying section 45 determines that the region of concern CR1 is the cancer MT. On the other hand, because the grayscale level of the region of concern CR2 is 10, the image-identifying section 45 determines that the region of concern CR2 is the benign tumor BT.

Based on the results of the above identification, the image-identifying section 45 determines whether the individual regions of concern CR1 and CR2 are the benign tumor BT or the cancer MT.

The image-identifying section 45, as shown in FIG. 1, outputs the identification result that the region of concern CR1 is the cancer MT and the region of concern CR2 is the benign tumor BT to the image-combining section 47 as affected-area-related data.

As shown in FIG. 1, on the other hand, the reflected-light-related data is input from the reflected-light image-acquiring section 25 to the reflected-light-image generating section 49.

Based on the reflected-light-related data, the reflected-light-image generating section 49 generates reflected-light image data. Reflected-light image data herein refers to a set of data related to a plurality of pixels, constituting a reflected-light image, that correspond to the individual image-acquisition devices of the reflected-light image-acquiring section 25. The data on the individual pixels in the reflected-light image data can be exemplified by data on the positions thereof in the reflected-light image and data on the grayscale levels thereof depending on the light intensity of reflected light.

The reflected-light image data is input from the reflected-light-image generating section 49 to the examination-distance determining section 51.

Figure 12:
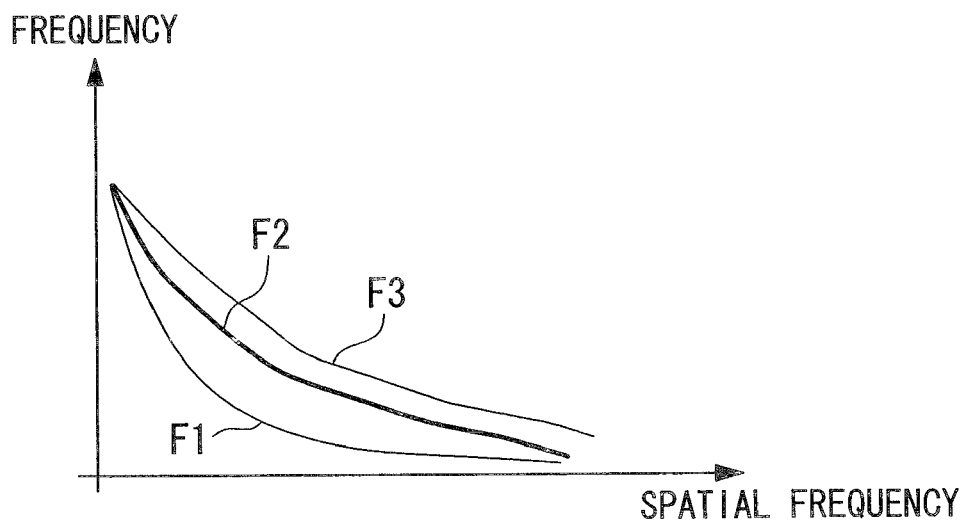
FIG. 12 is a graph showing the results of FFT processing by an examination-distance determining section in FIG. 1.

FIG. 12 is a graph showing the results of FFT processing by the examination-distance determining section in FIG. 1.

Based on the input reflected-light image data, the examination-distance determining section 51 determines the distance between the subject 3 and the distal end surface 27 of the insertion portion 5.

That is, the examination-distance determining section 51 executes fast Fourier transform (FFT) processing on the reflected-light image data to obtain the resolution of the reflected-light image. FIG. 12 is a graph showing the results of the FFT processing. In FIG. 12, spatial frequency is plotted along the horizontal axis, and frequency is plotted along the vertical axis. Graph F1 in FIG. 12 is a graph in the case where the distance between the subject 3 and the distal end surface 27 of the insertion portion 5 falls below 1 mm and the subject 3 is located beyond the depth of field. Graph F2 is a graph in the case where the distance between the subject 3 and the distal end surface 27 is 1 mm and the subject 3 is located at the limit of the depth of field. Graph F3 is a graph in the case where the distance between the subject 3 and the distal end surface 27 exceeds 1 mm and the subject 3 is located within the depth of field.

Using graph F2 as an FFT threshold, the examination-distance determining section 51 determines whether the distance between the subject 3 and the distal end surface 27 falls below or exceeds 1 mm. The examination-distance determining section 51 outputs the determination results, serving as examination-distance-related data, and the reflected-light image data to the image-combining section 47.

Although graph F2, where the distance between the subject 3 and the distal end surface 27 is 1 mm, is used as the FFT threshold in this embodiment, the data on the graph used as the FFT threshold is not limited to that in the case where the distance between the subject 3 and the distal end surface 27 is 1 mm because the depth of field varies depending on, for example, the selection of the image-acquisition lens 17.

The image-combining section 47 generates combined image data based on the fluorescence image data, the results of identification by the image-identifying section 45, the reflected-light image data, and the results of determination by the examination-distance determining section 51.

That is, the image-combining section 47 generates the combined image data based on the fluorescence image data and so on if the distance between the subject 3 and the distal end surface 27 is 1 mm or more according to the results of determination by the examination-distance determining section 51. Specifically, the image-combining section 47 executes processing for coloring the region of concern CR1 with a color representing the cancer MT and coloring the region of concern CR2 with a color representing the benign tumor BT and processing for incorporating the resultant image data into the combined image data. For the region other than the regions of concern CR1 and CR2, processing for incorporating the reflected-light image data into the combined image data is executed. The generated combined image data is output from the image-combining section 47 to the monitor 11. The monitor 11 displays the combined image based on the input combined image data.

On the other hand, the image-combining section 47 generates no combined image data if the distance between the subject 3 and the distal end surface 27 falls below 1 mm according to the results of determination by the examination-distance determining section 51.

Examination at an examination distance exceeds 2 mm is not assumed because fluorescence with sufficient brightness is not acquired at that distance or more. Hence, an image is generated only if the examination distance always falls within the assumed range.

The examination-distance determining section 51 may be omitted because, as described above, if the examination distance is 1 mm or less falls below 1 mm, it is possible to visually recognize that the subject 3 is located beyond the depth of field and the resolution is decreased.

In the above configuration, because the region-of-concern defining section 39, the neighboring-region defining section 41, and the image-operation section 43 are provided, the fluorescence endoscope 1 of this embodiment can distinguish the cancer MT from the normal tissue N and the benign tumor BT in a simple manner while reducing the effect of the distance from the subject 3.

The region-of-concern defining section 39 can define the regions of concern CR1 and CR2, which have higher fluorescence intensities than the surrounding region, based on the fluorescence image data. That is, as described above, because a fluorescent dye that emits fluorescence tends to accumulate in the cancer MT and fluorescence emitted from the cancer MT has high intensity, the region-of-concern defining section 39 can define regions that are possibly the cancer MT by defining the regions of concern CR1 and CR2 based on the fluorescence image data. Specifically, the region-of-concern defining section 39 can define regions whose grayscale levels related to fluorescence intensity are higher than the region-of-concern threshold in the fluorescence image data, as the regions of concern CR1 and CR2, which are possibly the cancer MT.

The neighboring-region defining section 41 can define the neighboring regions NR1 and NR2, which lie near the regions of concern CR1 and CR2, respectively. That is, the neighboring-region defining section 41 can define the neighboring regions NR1 and NR2, which are possibly the normal tissue N and are adjacent to the regions that are possibly the cancer MT.

Specifically, the neighboring-region defining section 41 can define regions surrounding the regions of concern CR1 and CR2 and having a thickness equal to the predetermined distance described above as the neighboring regions NR1 and NR2. Thus, the neighboring-region defining section 41 can always define regions adjacent to the regions of concern CR1 and CR2 as the neighboring regions NR1 and NR2.

The image-operation section 43 can generate corrected image data with a reduced effect of the distance from the subject 3 based on the ratios of the grayscale levels related to fluorescence intensity in the regions of concern CR1 and CR2 to the grayscale levels related to fluorescence intensity in the neighboring regions NR1 and NR2 adjacent to the regions of concern CR1 and CR2, respectively. Specifically, the image-operation section 43 can generate corrected image data that allows simultaneous evaluation of the grayscale levels related to the plurality of regions of concern CR1 and CR2, which differ in the distance between the light source unit 7 and the fluorescence image-acquiring section 23, by arithmetically determining the ratios of the grayscale levels related to the regions of concern CR1 and CR2 to the grayscale levels related to the neighboring regions NR1 and NR2, which have little difference from the regions of concern CR1 and CR2 in the distance between the light source unit 7 and the fluorescence image-acquiring section 23. As a result, the image-operation section 43 can generate corrected image data that allows distinguishing between the benign tumor BT and the cancer MT among the plurality of regions of concern CR1 and CR2.

The region of concern CR1 and the neighboring region NR1, as well as the region of concern CR2 and the neighboring region NR2, are at substantially equal distances to the endoscope distal end. Accordingly, the image-operation section 43 can generate corrected image data with a reduced effect of the distance between the subject 3 and the endoscope end surface 27 by determining the ratios of the grayscale levels related to fluorescence intensity in the regions of concern CR1 and CR2 and the neighboring regions NR1 and NR2 in a single set of fluorescence image data. Thus, because the luminance ratio between two regions that are at substantially equal distances in the same fluorescence image is determined, the fluorescence endoscope 1 of this embodiment can distinguish the cancer MT from the normal tissue N and the benign tumor BT in a simple manner without the need to use a reference-light image in addition to the fluorescence image, as in the techniques disclosed in Patent Documents 1 and 2 above.

Because the light source unit 7, the fluorescence image-acquiring section 23, and the fluorescence-image generating section 37 are provided, the fluorescence endoscope 1 of this embodiment can acquire the fluorescence image data.

The light source unit 7 can emit the light for irradiation of the subject 3. The fluorescence image-acquiring section 23 can acquire an image of the fluorescence contained in the return light originating from the subject 3. The fluorescence-image generating section 37 can generate the fluorescence image data based on the fluorescence-related data acquired by the fluorescence image-acquiring section 23.

The region-of-concern defining section 39, which defines the representative grayscale values of the regions of concern CR1 and CR2, and the neighboring-region defining section 41, which defines the representative grayscale values of the neighboring regions NR1 and NR2, are provided, and the image-operation section 43 generates the corrected image data based on the ratios of the representative grayscale values of the regions of concern CR1 and CR2 to the representative grayscale values of the neighboring regions NR1 and NR2, so that the fluorescence endoscope 1 of this embodiment can distinguish the cancer MT from the normal tissue N and the benign tumor BT with a reduced effect of the distance from the subject 3 with a simple configuration using fluorescence in a single wavelength band.

The region-of-concern defining section 39 calculates the representative grayscale values of the regions of concern CR1 and CR2 based on the grayscale levels related to the fluorescence intensity of the fluorescence emitted from the fluorescent dye, and the neighboring-region defining section 41 calculates the representative grayscale values of the neighboring regions NR1 and NR2 based on the grayscale levels related to the fluorescence intensity of autofluorescence, so that the cancer MT can be distinguished from the normal tissue N and the benign tumor BT while reducing the effect of the distance from the subject 3.

The region-of-concern defining section 39 can calculate the representative grayscale values of the regions of concern CR1 and CR2 based on the grayscale levels related to the fluorescence intensity of the fluorescence emitted from the fluorescent dye (chemical agent) introduced into the subject 3. That is, the representative grayscale values of the regions of concern CR1 and CR2 are calculated based on the grayscale levels related to the fluorescence intensity of the fluorescence emitted from the fluorescent dye. The region-of-concern defining section 39 can therefore define the representative grayscale values based on the grayscale levels related to the fluorescence intensity of the fluorescence emitted from the fluorescent dye, which is related to the cancer MT, as the representative values of the regions of concern CR1 and CR2, which are possibly the cancer MT, in which the fluorescent dye tends to accumulate.

The neighboring-region defining section 41 can calculate the representative grayscale values of the neighboring regions NR1 and NR2 based on the grayscale levels related to the intensity of the autofluorescence emitted from the subject 3. That is, the representative grayscale values of the neighboring regions NR1 and NR2 are calculated based on the grayscale levels related to the fluorescence intensity of the autofluorescence. The neighboring-region defining section 41 can therefore define the representative grayscale values based on the grayscale levels related to the fluorescence intensity of the autofluorescence, as the representative values of the neighboring regions NR1 and NR2, which are possibly the normal tissue N, in which the fluorescent dye does not tend to accumulate.

The image-operation section 43 can generate corrected image data with a reduced effect of the distance from the subject 3 based on the ratios of the calculated representative grayscale values of the regions of concern CR1 and CR2 to the calculated representative grayscale values of the neighboring regions NR1 and NR2 adjacent to the regions of concern CR1 and CR2. Specifically, the image-operation section 43 can generate corrected image data that allows simultaneous evaluation of the representative grayscale values of the plurality of regions of concern CR1 and CR2, which differ in the distance between the light source unit 7 and the fluorescence image-acquiring section 23, by arithmetically determining the ratios of the representative grayscale values of the regions of concern CR1 and CR2 to the representative grayscale values of the neighboring regions NR1 and NR2, which have little difference from the regions of concern CR1 and CR2 in the distance between the light source unit 7 and the fluorescence image-acquiring section 23. As a result, the image-operation section 43 can generate corrected image data that allows the cancer MT to be distinguished from the normal tissue N and the benign tumor BT among the plurality of regions of concern CR1 and CR2.

Thus, the fluorescence endoscope 1 of this embodiment can distinguish between the benign tumor BT and the cancer MT while reducing the effect of the distance from the subject 3.

Because the image-identifying section 45, the image-combining section 47, and the monitor 11 are provided, the fluorescence endoscope 1 of this embodiment can distinguish between the benign tumor BT and the cancer MT in a simple manner while reducing the effect of the distance from the subject 3.

The image-identifying section 45 can identify the cancer MT based on the corrected image data. That is, the image-identifying section 45 can identify the cancer MT based on corrected image data, generated by the image-operation section 43, with a reduced effect of the distance from the subject 3. Specifically, the image-identifying section 45 can identify, as the cancer MT, a region where the ratios of the calculated representative grayscale values of the regions of concern CR1 and CR2 to the calculated representative grayscale values of the neighboring regions NR1 and NR2 are higher than a predetermined threshold. With the ratios of the representative grayscale values of the regions of concern CR1 and CR2 to the representative grayscale values of the neighboring regions NR1 and NR2, the image-identifying section 45 can distinguish between the benign tumor BT and the cancer MT while reducing the effect of the distance from the subject 3.

The image-combining section 47 can combine the corrected image data and the cancer MT identified by the image-identifying section 45 to generate the combined image data. That is, the image-combining section 47 can generate combined image data in which the cancer MT is distinguished from the normal tissue N and the benign tumor BT.

The monitor 11 can display the combined image based on the combined image data. Hence, the operator of the fluorescence endoscope 1 of this embodiment can view a combined image displayed on the monitor 11 in which the cancer MT is distinguished from the normal tissue N and the benign tumor BT. That is, the operator can easily distinguish the cancer MT from the normal tissue N and the benign tumor BT.

Because the reflected-light image-acquiring section 25, the reflected-light-image generating section 49, and the image-combining section 47 are provided, the fluorescence endoscope 1 of this embodiment can distinguish the cancer MT from the normal tissue N and the benign tumor BT in a simple manner.

The reflected-light image-acquiring section 25 can acquire an image of the reflected light, for example, white light, contained in the return light from the subject 3.

The reflected-light-image generating section 49 can generate the image related to the reflected light other than fluorescence, namely, the reflected-light image data, based on the reflected-light-related data acquired by the reflected-light image-acquiring section 25.

The image-combining section 47 can combine the reflected-light image data with the fluorescence image data. For example, if the reflected light is white light, the cancer MT can be more easily distinguished from the normal tissue N and the benign tumor BT by combining the reflected-light image data, which is the same image as viewed by the naked eye, with the fluorescence image data, in which the cancer MT can be easily distinguished from the normal tissue N and the benign tumor BT.

Because the insertion portion 5 and the light guide 13 are provided, the cancer MT can be distinguished from the normal tissue N and the benign tumor BT in the body cavity of the subject 3.

The insertion portion 5 can be inserted into the body cavity of the subject 3. The light guide 13 can guide the light emitted from the light source unit 7 through the insertion portion 5 to the distal end of the insertion portion 5 and cause the light to exit toward the subject 3. Thus, fluorescence can be emitted from the normal tissue N, the benign tumor BT, and the cancer MT present in the body cavity of the subject 3, so that the cancer MT can be distinguished from the normal tissue N and the benign tumor BT in the body cavity of the subject 3 based on the fluorescence intensity of the fluorescence.

The region-of-concern threshold T may be a predetermined value between the maximum value of the grayscale levels related to the normal tissue N and the minimum value of the grayscale levels related to the benign tumor BT, as in the above embodiment, or may be the maximum value of the grayscale levels related to the normal tissue N multiplied by a predetermined coefficient, the intermediate value between the maximum value of the grayscale levels related to the normal tissue N and the minimum value of the grayscale levels related to the benign tumor BT, or the maximum value of the grayscale levels related to the cancer MT divided by a predetermined coefficient; there is no particular limitation.

The case where the region-of-concern threshold T is the maximum value of the grayscale levels related to the normal tissue N multiplied by a predetermined coefficient can be exemplified by the case where the region-of-concern threshold T is twice the maximum value, 20, of the grayscale levels related to the normal tissue N, namely, 40.

The case where the region-of-concern threshold T is the intermediate value between the maximum value of the grayscale levels related to the normal tissue N and the minimum value of the grayscale levels related to the benign tumor BT can be exemplified by the case where the region-of-concern threshold T is the intermediate value between the maximum value, 20, of the grayscale levels related to the normal tissue N and the minimum value, 50, of the grayscale levels related to the benign tumor BT, namely, 35.

Furthermore, the case where the region-of-concern threshold T is the maximum value of the grayscale levels related to the cancer MT divided by a predetermined coefficient can be exemplified by the case where the region-of-concern threshold T is the maximum value, 500, of the grayscale levels related to the cancer MT divided by 20, namely, 25.

Figure 13:
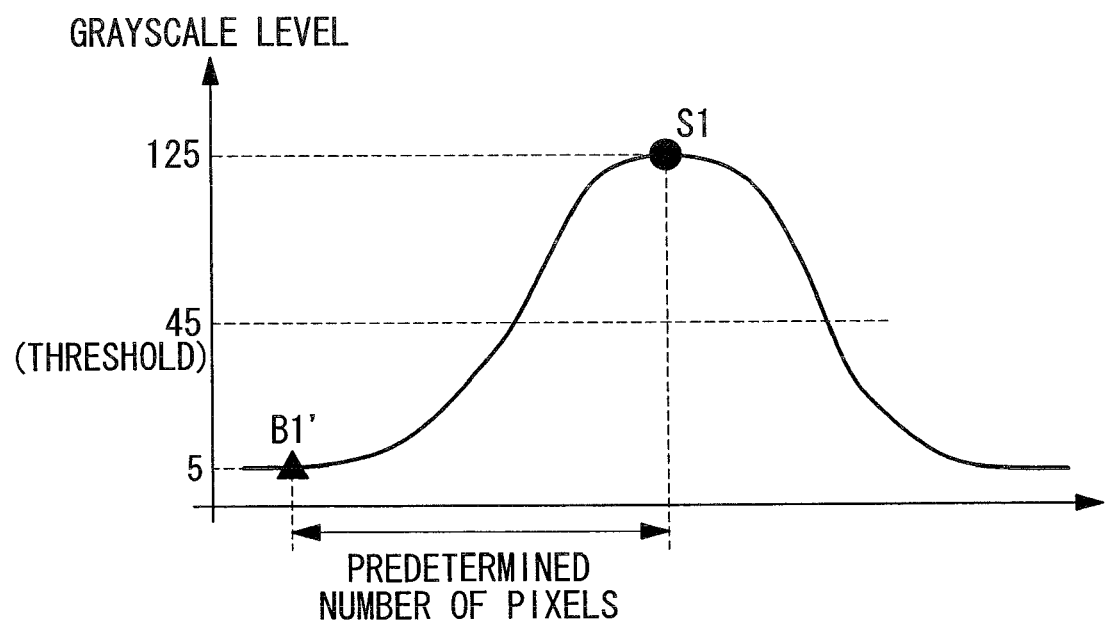
FIG. 13 is another graph showing the distribution of the grayscale levels of the individual pixels on the profile P1 in FIG. 7.
Figure 14:
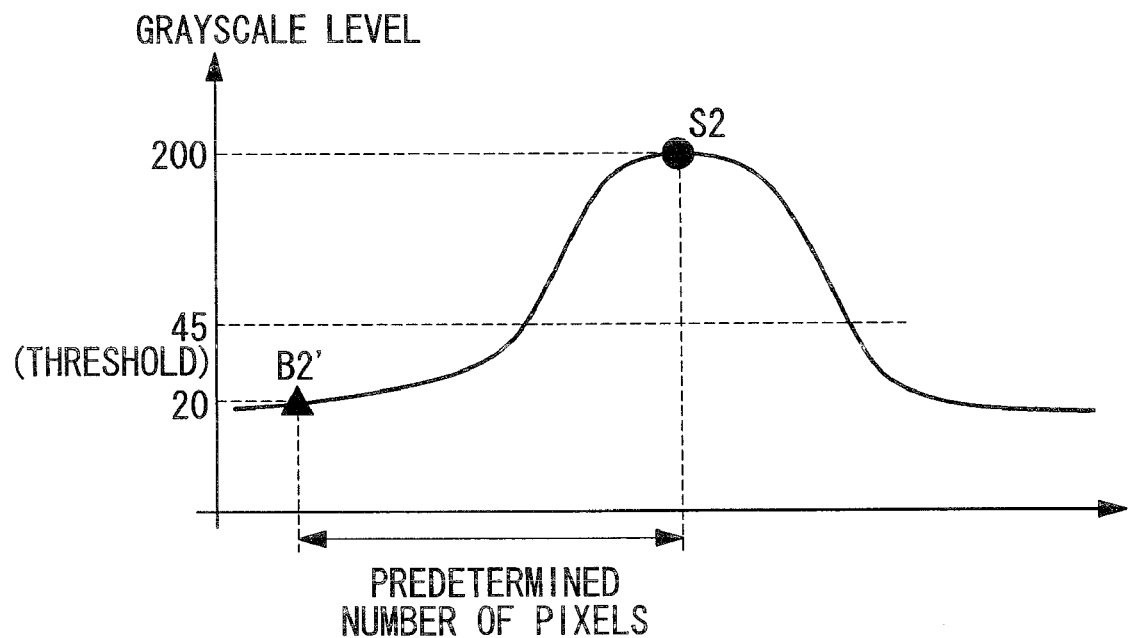
FIG. 14 is another graph showing the distribution of the grayscale levels of the individual pixels on the profile P2 in FIG. 7.

FIG. 13 is another graph showing the distribution of the grayscale levels of the individual pixels on the profile P1 in FIG. 7. FIG. 14 is another graph showing the distribution of the grayscale levels of the individual pixels on the profile P2 in FIG. 7.

While the pixels separated from the pixels with the grayscale level equal to the region-of-concern threshold in the regions of concern CR1 and CR2 by a predetermined number of pixels may be defined as the representative pixels B1 and B2 of the neighboring regions NR1 and NR2, as in the above embodiment, the pixels separated from the representative pixels (predetermined positions) S1 and S2 of the regions of concern CR1 and CR2 along the profiles P1 and P2 by a predetermined number of pixels may be defined as representative pixels B1' and B2', as shown in FIGS. 13 and 14; there is no particular limitation. In this case, the neighboring regions NR1 and NR2 are the regions from the pixels with the grayscale level equal to the region-of-concern threshold in the regions of concern CR1 and CR2 to the representative pixels B1' and B2'.

In this operation method, because the neighboring-region defining section 41 defines, as the neighboring regions NR1 and NR2, the regions from the boundaries of the regions of concern CR1 and CR2 to the representative pixels B1' and B2' separated from the representative pixels S1 and S2 in the regions of concern CR1 and CR2 by the predetermined distance, the neighboring-region defining section 41 can define regions adjacent to the regions of concern CR1 and CR2 as the neighboring regions NR1 and NR2.

The neighboring-region defining section 41 can define, as the neighboring regions NR1 and NR2, the regions from the boundaries of the regions of concern CR1 and CR2 to the representative pixels B1' and B2' separated from the representative pixels S1 and S2 in the regions of concern CR1 and CR2 by the predetermined distance. That is, the neighboring-region defining section 41 can define regions surrounding the regions of concern CR1 and CR2 as the neighboring regions NR1 and NR2 by defining the representative pixels B1' and B2' separated from the representative pixels S1 and S2 by the predetermined distance as the boundaries with the normal tissue N. Thus, the neighboring-region defining section 41 can always define regions adjacent to the regions of concern CR1 and CR2 as the neighboring regions NR1 and NR2.

The method of defining the boundaries between the neighboring regions NR1 and NR2 and the normal tissue N based on the distance from the representative pixels S1 and S2 of the regions of concern CR1 and CR2 allows easier definition than the method of definition based on the distance from the boundaries with the regions of concern CR1 and CR2.

While the pixels with the maximum grayscale levels in the regions of concern CR1 and CR2 may be extracted as the representative pixels S1 and S2 of the regions of concern CR1 and CR2, as in the above embodiment, the pixels corresponding to the centers of mass in the regions of concern CR1 and CR2 may be extracted as the representative pixels S1 and S2; there is no particular limitation. The centers of mass may be determined from the centers of ellipses or circles inscribed in the regions of concern CR1 and CR2 or from the centers of mass of inscribed triangles or polygons; there is no particular limitation.

Figure 15:
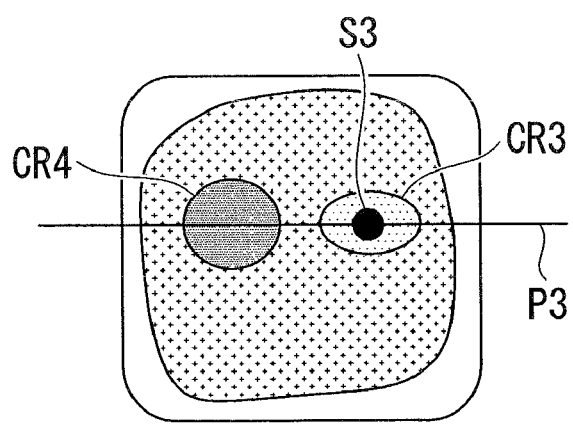
FIG. 15 is a diagram illustrating another profile set by the neighboring-region defining section in FIG. 1.
Figure 16:
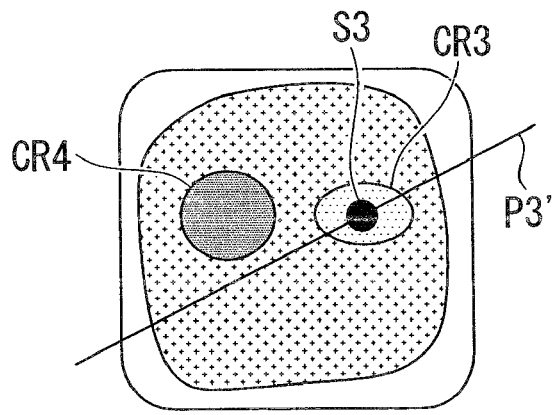
FIG. 16 is a diagram illustrating still another profile set by the neighboring-region defining section in FIG. 1.
Figure 17:
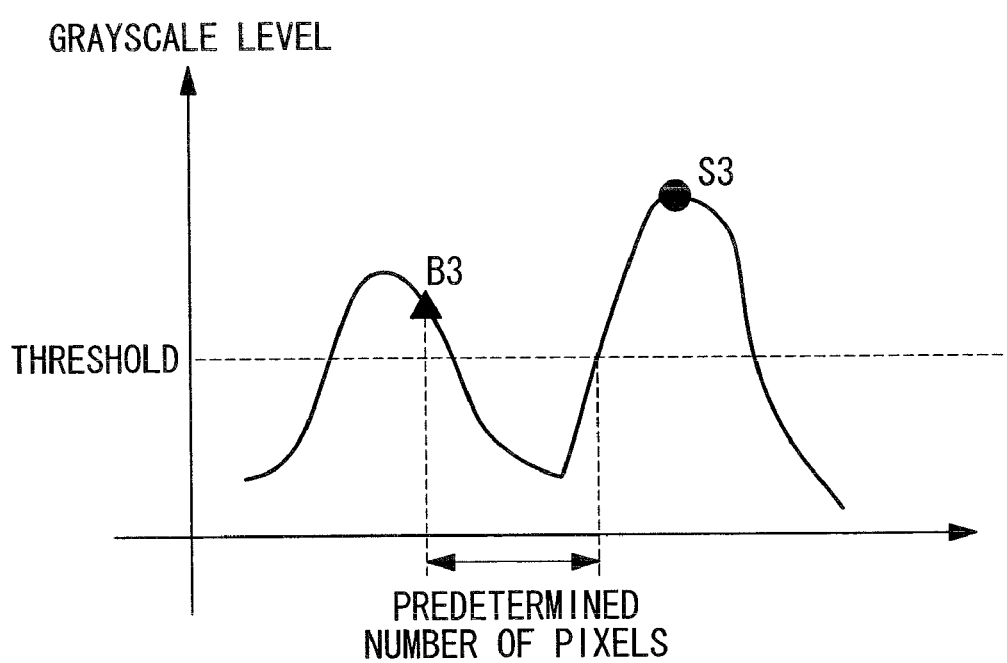
FIG. 17 is a graph showing the distribution of the grayscale levels of individual pixels on a profile P3 in FIG. 15.
Figure 18:
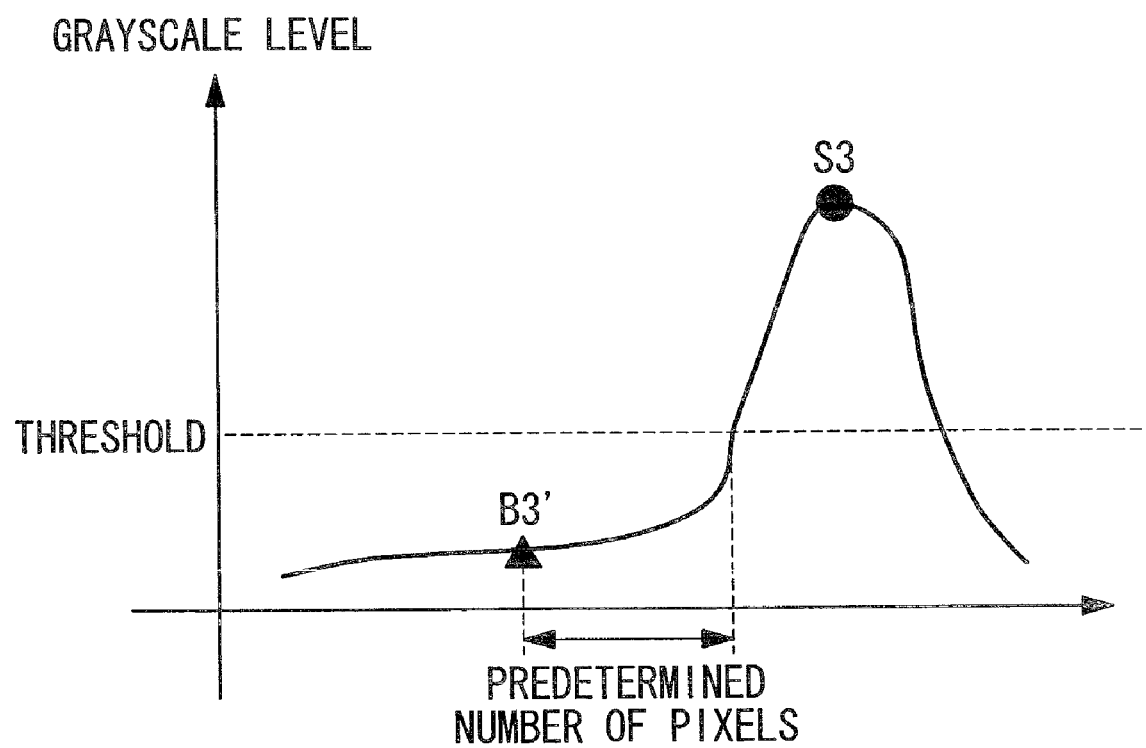
FIG. 18 is a graph showing the distribution of the grayscale levels of individual pixels on a profile P3' in FIG. 16.

FIG. 15 is a diagram illustrating another profile set by the neighboring-region defining section in FIG. 1. FIG. 16 is a diagram illustrating still another profile set by the neighboring-region defining section in FIG. 1. FIG. 17 is a graph showing the distribution of the grayscale levels of the individual pixels on a profile P3 in FIG. 15. FIG. 18 is a graph showing the distribution of the grayscale levels of the individual pixels on a profile P3' in FIG. 16.

No problem arises if, as in the above embodiment, none of the profiles P1 and P2 set by the neighboring-region defining section 41 crosses the other region of concern CR1 or CR2; as shown in FIG. 15, if the profile P3, set for a region of concern CR3, crosses an adjacent region of concern CR4, the new profile P3' may be set, as shown in FIG. 16.

That is, if the profile P3 crosses the adjacent region of concern CR4, the grayscale levels of the individual pixels on the profile P3 form a distribution shown in FIG. 17. In this case, if a pixel separated from the boundary pixel of the region of concern CR3 by a predetermined number of pixels is defined as a representative pixel B3, the representative pixel B3 is inappropriately included in the region of concern CR4. Hence, the neighboring-region defining section 41 sets the new profile P3', which does not cross the adjacent region of concern CR4. The grayscale levels of the individual pixels on the profile P3' form a distribution shown in FIG. 18. In this case, a pixel separated from the boundary pixel of the region of concern CR3 by a predetermined number of pixels is defined as a representative pixel B3'. Setting the representative pixel B3' in this way allows appropriate setting of the representative pixel B3'.

First Modification of First Embodiment

Next, a first modification of the first embodiment of the present invention will be described with reference to FIGS. 19 to 21.

The basic configuration of a fluorescence endoscope of this modification is similar to that of the first embodiment but differs therefrom in the method for distance determination by the examination-distance determining section. In this modification, therefore, only the method for distance determination in the examination-distance determining section will be described using FIGS. 19 to 21, and a description of other components and so on will be omitted.

Figure 19:
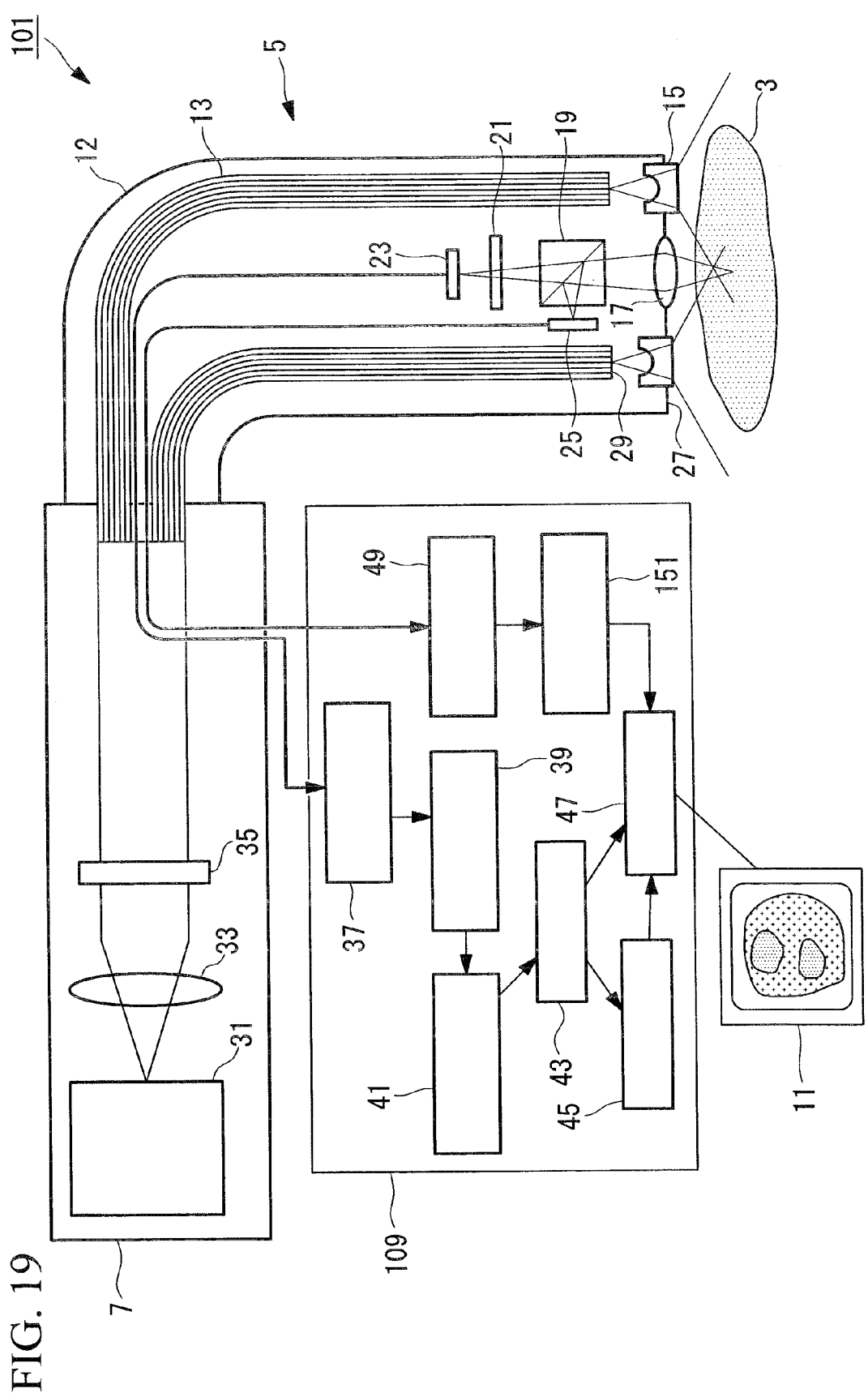
FIG. 19 is a schematic diagram illustrating the configuration of a fluorescence endoscope in a first modification of the first embodiment of the present invention.

FIG. 19 is a schematic diagram illustrating the configuration of the fluorescence endoscope in this modification.

The same components as in the first embodiment are indicated by the same reference signs, and a description thereof will be omitted.

As shown in FIG. 19, an image-generating unit 109 of a fluorescence endoscope 101 includes a fluorescence-image generating section 37, a region-of-concern defining section 39, a neighboring-region defining section 41, an image-operation section 43, an image-identifying section 45, an image-combining section 47, a reflected-light-image generating section 49, and an examination-distance determining section 151.

The examination-distance determining section 151 determines the examination distance based on reflected-light image data. The reflected-light image data is input from the reflected-light-image generating section 49 to the examination-distance determining section 151. The reflected-light image data and data related to the examination distance are output from the examination-distance determining section 151 to the image-combining section 47.

Next, examination of the subject 3 and distinguishing between normal and affected areas with the fluorescence endoscope 101 having the above configuration will be described.

The case where the relative positional relationship between the subject 3 and the insertion portion 5 is the same as the positional relationship described in the first embodiment will be described herein.

The process in which the fluorescence endoscope 101 irradiates the subject 3 with excitation light and illumination light and inputs corrected image data and the results of distinguishing between the benign tumor BT and the cancer MT for fluorescence contained in return light to the image-combining section 47 is similar to that of the first embodiment; therefore, a description thereof will be omitted.

The process in which reflected-light image data for reflected light contained in the return light is input to the examination-distance determining section 151 is similar to that of the first embodiment; therefore, a description thereof will be omitted.

The method of determining the distance between the subject 3 and the distal end surface 27 of the insertion portion 5 in the examination-distance determining section 151 will be described herein.

Figure 20:
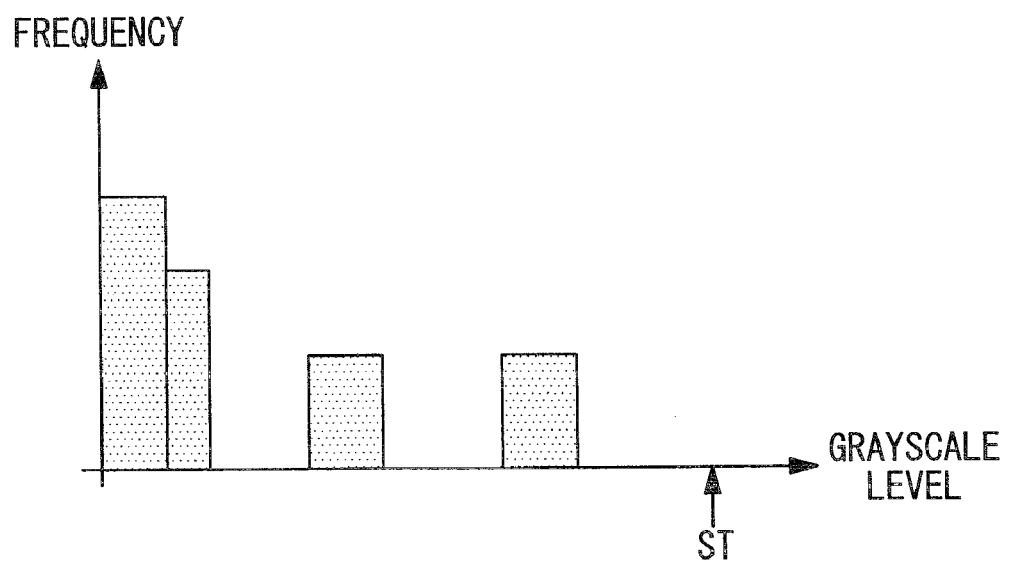
FIG. 20 is a graph showing a modification of the frequency distribution of grayscale levels in reflected-light image data analyzed by the examination-distance determining section in FIG. 19.

FIG. 20 is a graph showing an example of the frequency distribution of the grayscale levels in the reflected-light image data analyzed by the examination-distance determining section in FIG. 19. FIG. 21 is a graph showing another example of the frequency distribution of the grayscale levels in the reflected-light image data analyzed by the examination-distance determining section in FIG. 19.

The examination-distance determining section 151 determines the distance between the subject 3 and the distal end surface 27 of the insertion portion 5 based on the number of pixels with saturated grayscale levels in the input reflected-light image data.

Figure 21:
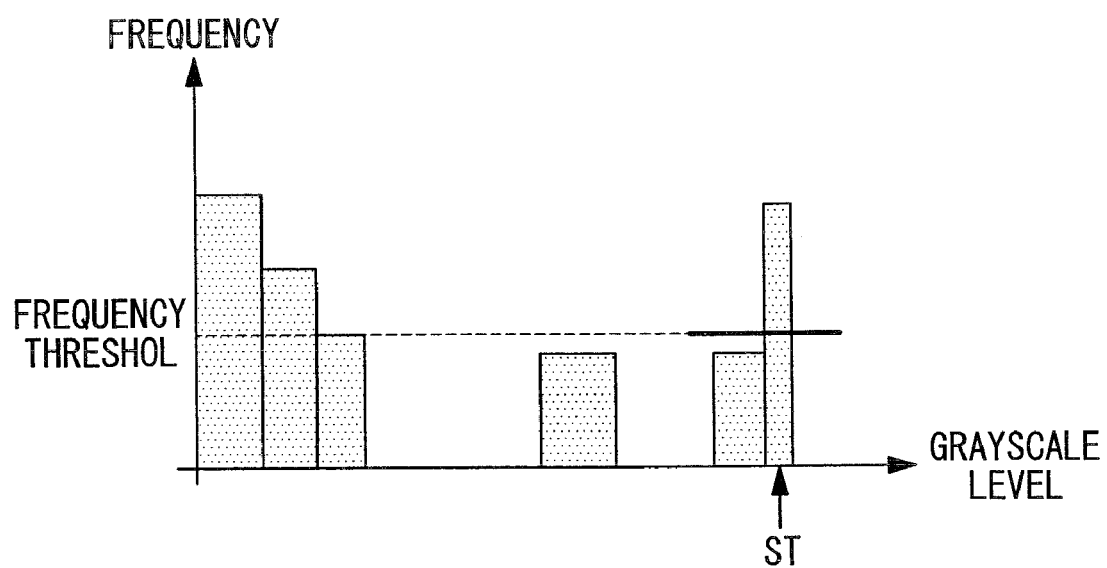
FIG. 21 is a graph showing another modification of the frequency distribution of grayscale levels in the reflected-light image data analyzed by the examination-distance determining section in FIG. 19.

That is, the examination-distance determining section 151 extracts the numbers (frequencies) of pixels at the individual grayscale levels from the reflected-light image data and generates a graph showing the frequency distribution of the grayscale levels, as shown in FIGS. 20 and 21.

If the distance between the subject 3 and the distal end surface 27 exceeds 1 mm, the graph showing the frequency distribution of the grayscale levels is as shown in FIG. 20. As shown in FIG. 20, the frequency distribution of the grayscale levels extends within a grayscale range lower than a grayscale saturation point ST.

In this case, the examination-distance determining section 151 determines that the distance between the subject 3 and the distal end surface 27 exceeds 1 mm.

On the other hand, if the distance between the subject 3 and the distal end surface 27 falls below 1 mm, the graph showing the frequency distribution of the grayscale levels is as shown in FIG. 21. As shown in FIG. 21, the frequency distribution of the grayscale levels extends over a grayscale range including the grayscale saturation point ST.

In this case, if the frequency at the grayscale saturation point ST is equal to or higher than a predetermined frequency threshold, the examination-distance determining section 151 determines that the distance between the subject 3 and the distal end surface 27 falls below 1 mm. If the frequency at the grayscale saturation point ST falls below the predetermined frequency threshold, the distance between the subject 3 and the distal end surface 27 is determined to exceed 1 mm.

The examination-distance determining section 151 outputs the above determination results and the reflected-light image data to the image-combining section 47.

The operation and so on in the image-combining section 47 and the subsequent sections are similar to those of the first embodiment; therefore, a description thereof will be omitted.

This method involves a simpler algorithm than the method based on FFT.

The examination-distance determining section 151 may determine the distance between the subject 3 and the distal end surface 27 based on the reflected-light image data, as in the above modification, or may similarly determine the distance between the subject 3 and the distal end surface 27 based on the fluorescence image data; there is no particular limitation.

Second Modification of First Embodiment

Next, a second modification of the first embodiment of the present invention will be described with reference to FIGS. 22 to 25.

The basic configuration of a fluorescence endoscope of this modification is similar to that of the first embodiment but differs therefrom in the configuration of the insertion portion and the image-generating unit. In this modification, therefore, only the insertion portion and the image-generating unit, and the periphery thereof, will be described using FIGS. 22 to 25, and a description of other components and so on will be omitted.

Figure 22:
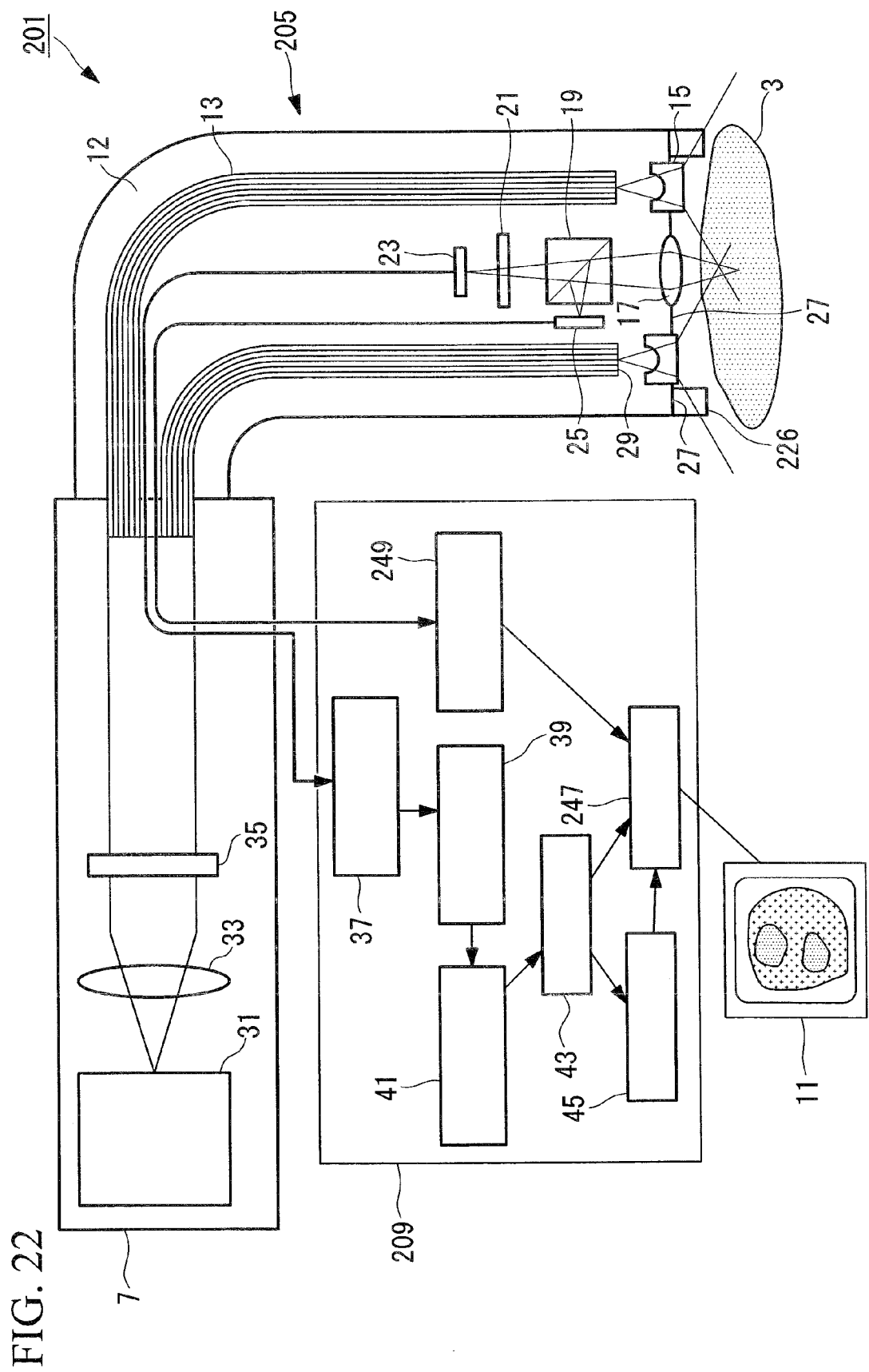
FIG. 22 is a schematic diagram illustrating the configuration of a fluorescence endoscope in a second modification of the first embodiment of the present invention.

FIG. 22 is a schematic diagram illustrating the configuration of the fluorescence endoscope in this modification.

The same components as in the first embodiment are indicated by the same reference signs, and a description thereof will be omitted.

As shown in FIG. 22, a fluorescence endoscope 201 includes an insertion portion 205 for insertion into the body cavity of a subject 3, a light source unit 7, an image-generating unit 209, and a monitor 11.

The insertion portion 205 includes an outer tube 12, a light guide 13, an illumination lens 15, an image-acquisition lens 17, a dichroic prism 19, an excitation-light cut filter 21, a fluorescence image-acquiring section 23, a reflected-light image-acquiring section 25, and a distal protrusion 226.

The distal protrusion 226 limits the minimum distance between the distal end surface 27 of the insertion portion 205 and the subject 3.

The distal protrusion 226 is a member extending from the distal end surface 27 of the insertion portion 205 in the direction in which excitation light and illumination light exit. The distal protrusion 226 is formed in a substantially cylindrical shape with a length equal to a height of about 1 mm from the distal end surface 27. The inner diameter of the distal protrusion 226 is determined so that the illumination lens 15 can be disposed inside the distal protrusion 226.

The image-generating unit 209 includes a fluorescence-image generating section 37, a region-of-concern defining section 39, a neighboring-region defining section 41, an image-operation section 43, an image-identifying section 45, an image-combining section 247, and a reflected-light-image generating section 249.

The image-combining section 247 combines corrected image data, an identified affected area, and reflected-light image data to generate combined image data. The corrected image data is input from the image-operation section 43 to the image-combining section 247, the data related to the affected area is input from the image-identifying section 45 to the image-combining section 247, and the reflected-light image data is input from the reflected-light-image generating section 249 to the image-combining section 247. The combined image data is output from the image-combining section 247 to the monitor 11.

The reflected-light-image generating section 249 generates the reflected-light image data based on reflected-light-related data acquired by the reflected-light image-acquiring section 25. The reflected-light-related data is input from the reflected-light image-acquiring section 25 to the reflected-light-image generating section 249. The reflected-light image data is output from the reflected-light-image generating section 249 to the image-combining section 247.

Next, examination of the subject 3 and distinguishing between normal and affected areas with the fluorescence endoscope 201 having the above configuration will be described.

Figure 23:
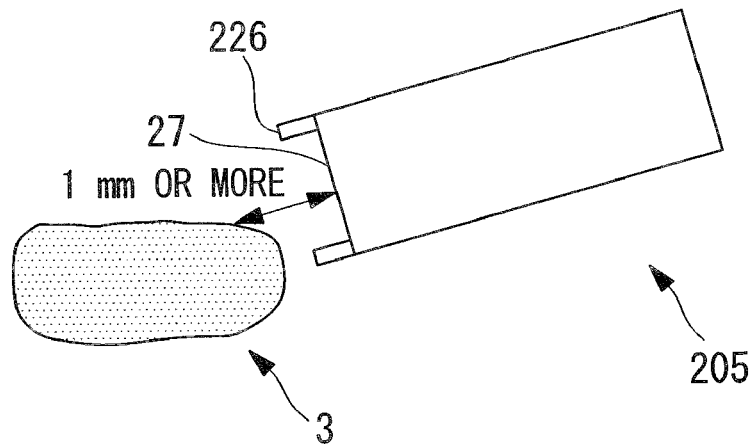
FIG. 23 is a schematic diagram showing a modification of the relative positional relationship between a subject and an insertion portion in this modification.
Figure 24:
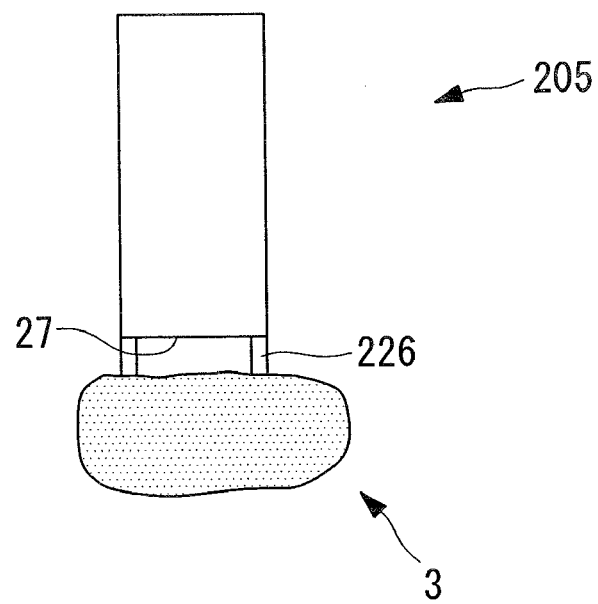
FIG. 24 is a schematic diagram showing another modification of the relative positional relationship between the subject and the insertion portion in this modification.

FIG. 23 is a schematic diagram showing a modification of the relative positional relationship between the subject 3 and the insertion portion 205 in this modification. FIG. 24 is a schematic diagram showing another modification of the relative positional relationship between the subject 3 and the insertion portion 205 in this modification.

As shown in FIG. 23, if the insertion portion 205 approaches the subject 3 from above and at an inclination relative to the subject 3, the distal protrusion 226 contacts the subject 3 first. Hence, the minimum distance between the distal end surface 27 of the insertion portion 205 and the subject 3 is at least 1 mm or more. As shown in FIG. 24, if the insertion portion 205 approaches the subject 3 from above the subject 3, the distal protrusion 226 contacts the subject 3. Hence, the distance between the distal end surface 27 and the subject 3 is at least 1 mm or more.

That is, the distance between the distal end surface 27 and the subject 3 is always 1 mm or more.

The process in which the fluorescence endoscope 201 irradiates the subject 3 with excitation light and illumination light and inputs corrected image data and the results of distinguishing between the benign tumor BT and the cancer MT for fluorescence contained in return light to the image-combining section 247 is similar to that of the first embodiment; therefore, a description thereof will be omitted.

For reflected light contained in the return light, this modification differs from the first embodiment only in that the reflected-light image data generated by the reflected-light-image generating section 249 is input to the image-combining section 247, and is similar in the other configuration to the first embodiment; therefore, a description thereof will be omitted.

The image-combining section 247 generates combined image data based on fluorescence image data, the results of identification by the image-identifying section 45, and the reflected-light image data. That is, the image-combining section 247 differs from that of the first embodiment only in that the image-combining section 247 always generates the combined image data based on the fluorescence image data and so on, and is similar in the other configuration to that of the first embodiment; therefore, a description thereof will be omitted.

Figure 25:
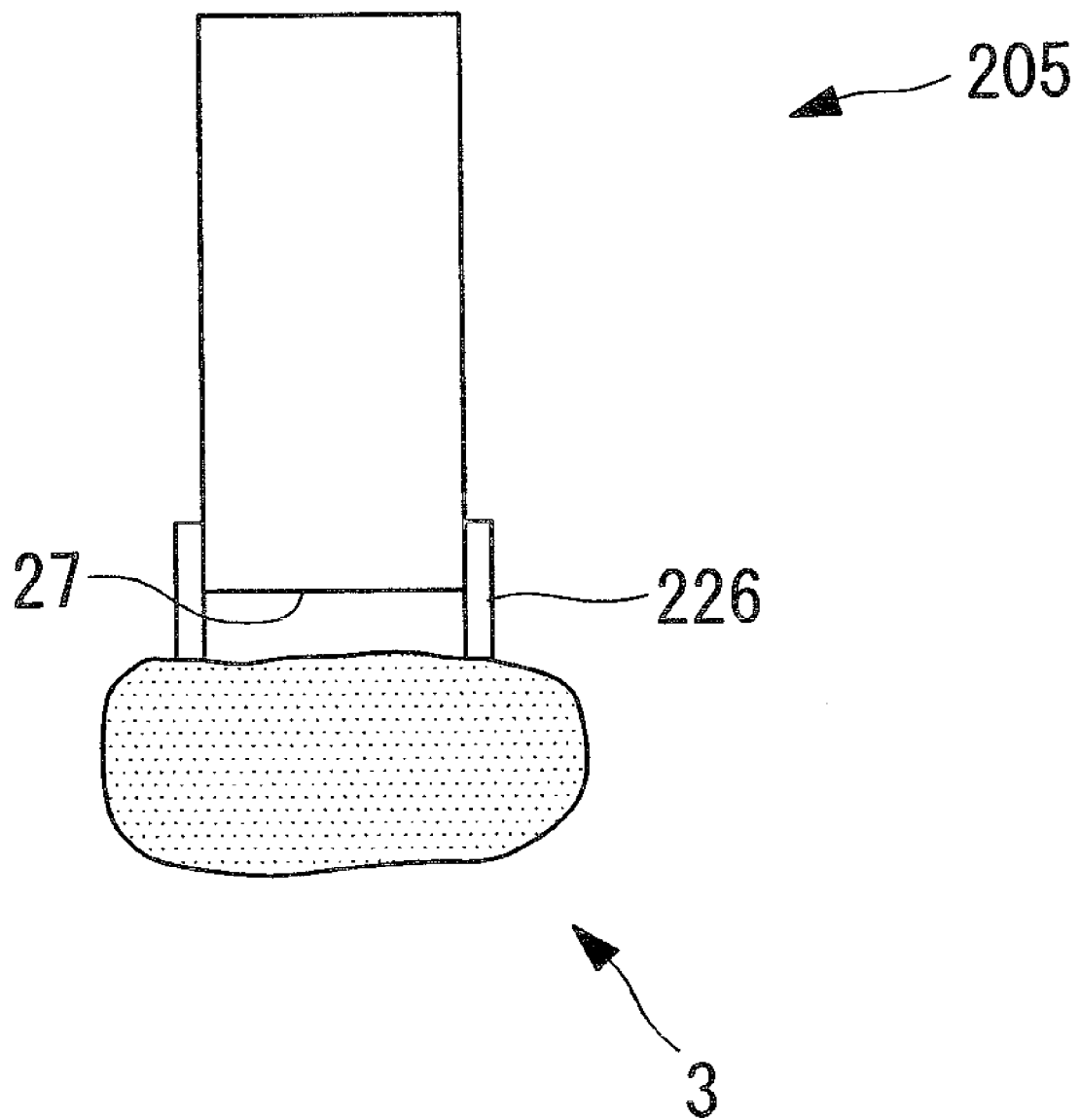
FIG. 25 is a schematic diagram showing another example of the configuration of a distal protrusion in FIG. 22.

FIG. 25 is a schematic diagram showing another example of the configuration of the distal protrusion in FIG. 22.

The distal protrusion 226 may be provided on the distal end surface 27 of the insertion portion 205, as in the above modification, or may be formed in the shape of a cap surrounding the outer tube 12 of the insertion portion 205, as shown in FIG. 25; there is no particular limitation.

With this modification, no distance-determining section is required, thus simplifying the image-generating unit 209.

Although the case where the assumed examination distance for the definition of the regions of concern CR ranges from 1 to 2 mm, that is, the case where the upper limit of the examination distance is twice the lower limit thereof, has been described in this embodiment, the assumed examination distance can be changed depending on, for example, the size of the subject 3, namely, the size of a duct in the body cavity, and the type of fluorescent dye used.

That is, the examination distance may be changed depending on the size of the duct in the body cavity so that the ratio of the upper limit of the examination distance to the lower limit thereof remains constant. For example, if the subject 3 is a human esophagus, stomach, or intestine, the assumed examination distance can be set to the range of, for example, 7.5 to 15 mm or 10 to 20 mm.

The lower limit of the examination distance is preferably a distance equal to or more than half the distance from the distal end surface 27 of the insertion portion 5 to the best focus position (in-focus position) so that an image of the subject 3 is formed on the light-receiving surface of the fluorescence image-acquiring section 23.

The examination range is preferably changed depending on the type of fluorescent dye because the luminances of fluorescence emitted from the benign tumor BT and the cancer MT, which is an affected area, vary with the type of fluorescent dye. Because the displayed grayscale level varies inversely with the square of the actual distance, if the fluorescent dye used is such that the actual luminances of the fluorescence emitted from the benign tumor BT and the cancer MT in the subject 3 are $L^2$ times higher than the actual luminance of fluorescence from the normal tissue N, the region-of-concern defining section 39 sets the upper limit of the examination distance to a distance less than or equal to L times the lower limit thereof.

The above point will be described with a specific example.

If the actual luminances of the fluorescence from the benign tumor BT and the cancer MT are at least ten times higher than the actual luminance of the fluorescence from the normal tissue N, the region-of-concern defining section 39 sets the examination distance to the range of 1 to 3 mm so that the upper limit of the examination distance is three times the lower limit thereof.

With the upper limit set as above, the grayscale level of the benign tumor BT or the cancer MT does not overlap that of the normal tissue N. Accordingly, setting the region-of-concern threshold T between grayscale levels of 45 and 60 allows distinguishing between the region of the normal tissue N and the regions including the benign tumor BT and the cancer MT, which is an affected area, even if the distance between the subject 3 and the distal end surface 27 varies between 1 mm and 3 mm.

As a result, even if the type of fluorescent dye used is changed, the region-of-concern defining section 39 can reliably define a region that is possibly an affected area as a region of concern by setting an appropriate examination distance.

Second Embodiment

Next, a second embodiment of the present invention will be described with reference to FIGS. 26 to 32.

The basic configuration of a fluorescence endoscope of this embodiment is similar to that of the first embodiment but differs therefrom in the method for defining a region of concern. In this embodiment, therefore, only the method, and the periphery thereof, for defining a region of concern will be described using FIGS. 26 to 32, and a description of other components and so on will be omitted.

Figure 26:
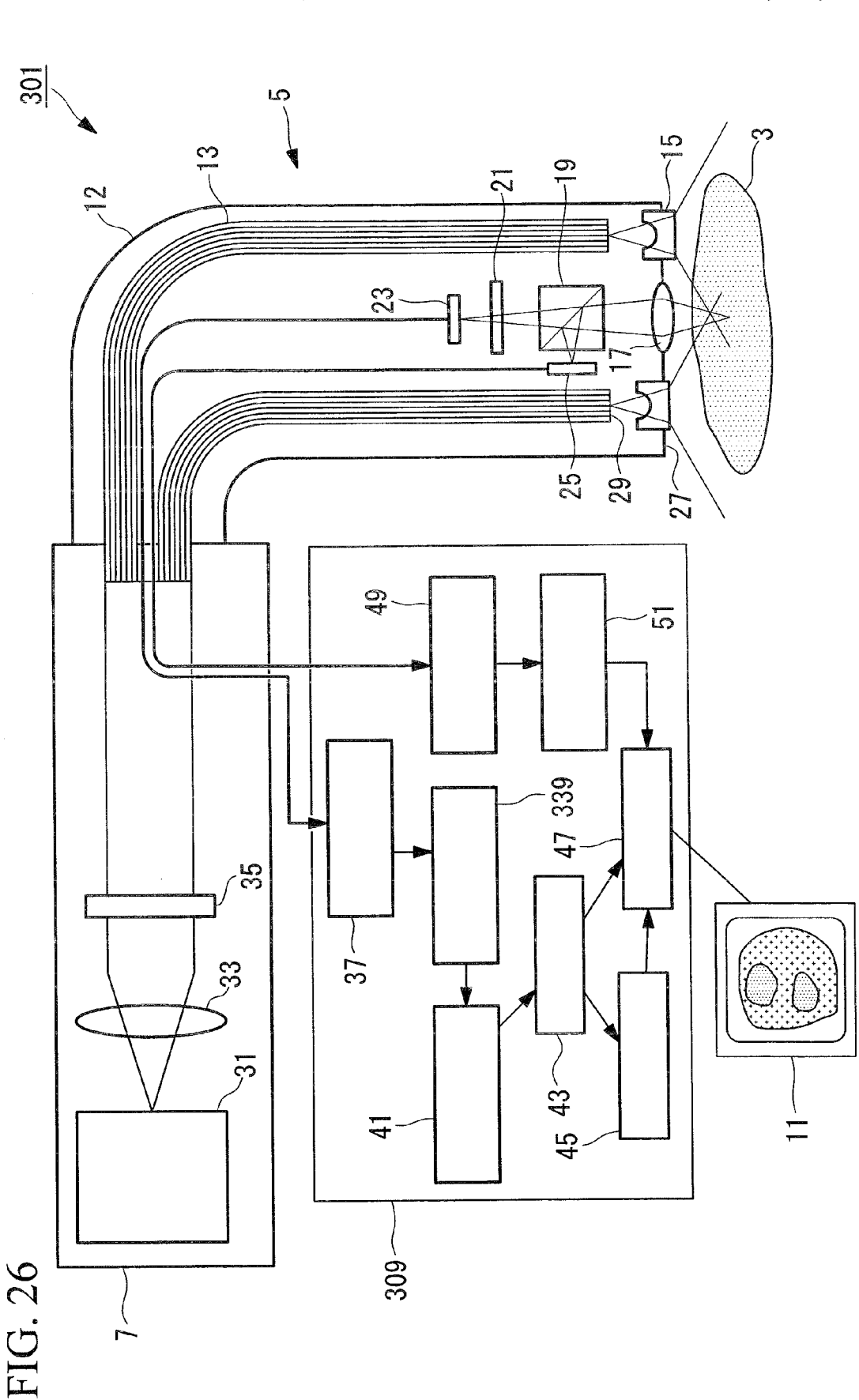
FIG. 26 is a schematic diagram illustrating the configuration of a fluorescence endoscope according to a second embodiment of the present invention.

FIG. 26 is a schematic diagram illustrating the configuration of the fluorescence endoscope according to this embodiment.

The same components as in the first embodiment are indicated by the same reference signs, and a description thereof will be omitted.

As shown in FIG. 26, a fluorescence endoscope 301 includes an insertion portion 5 for insertion into the body cavity of a subject 3, a light source unit 7, an image-generating unit 309, and a monitor 11.

The image-generating unit 309 includes a fluorescence-image generating section 37, a region-of-concern defining section (region-of-concern defining section, region-of-concern representative-value calculating section) 339, a neighboring-region defining section 41, an image-operation section 43, an image-identifying section 45, an image-combining section 47, a reflected-light-image generating section 49, and an examination-distance determining section 51.

The region-of-concern defining section 339 defines a region of concern based on fluorescence image data.

The fluorescence image data is input from the fluorescence-image generating section 37 to the region-of-concern defining section 339. Data related to the region of concern and the fluorescence image data are output from the region-of-concern defining section 339 to the neighboring-region defining section 41.

Next, examination of the subject 3 and distinguishing between normal and affected areas with the fluorescence endoscope 301 having the above configuration will be described.

The case where the relative positional relationship between the subject 3 and the insertion portion 5 is the same as the positional relationship described in the first embodiment will be described herein.

The process in which the fluorescence endoscope 301 irradiates the subject 3 with excitation light and illumination light and inputs fluorescence image data for fluorescence contained in return light to the region-of-concern defining section 339 is similar to that of the first embodiment; therefore, a description thereof will be omitted.

Figure 27:
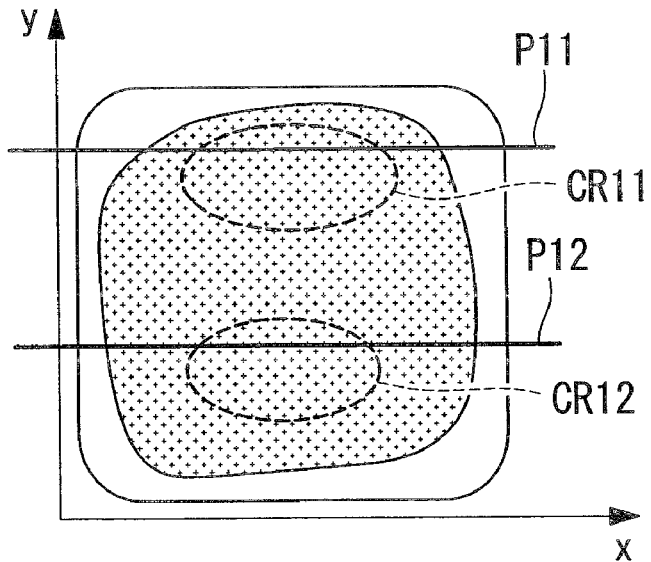
FIG. 27 is a diagram illustrating coordinate axes set in fluorescence image data by a region-of-concern defining section in FIG. 26.
Figure 28:
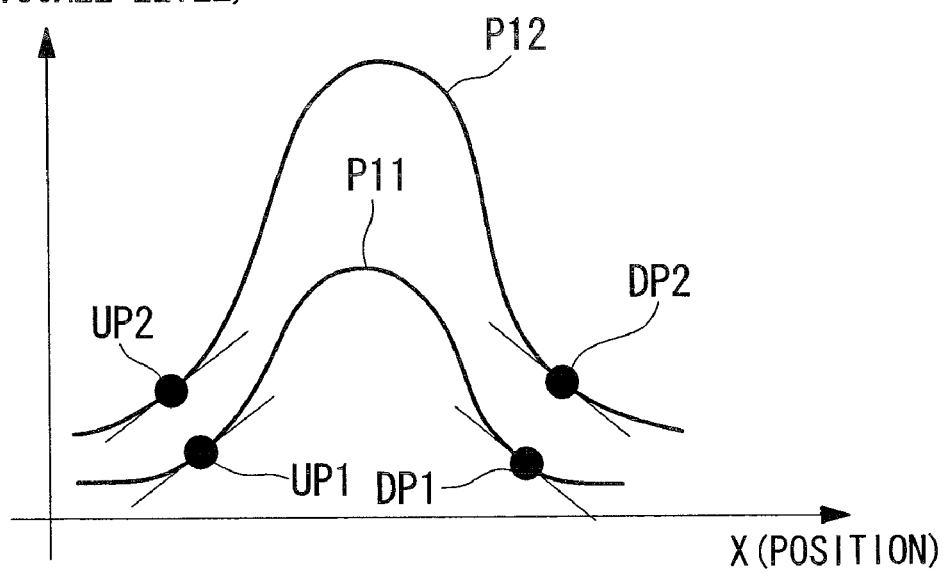
FIG. 28 is a graph showing variations in pixel grayscale level along profiles in FIG. 27.

FIG. 27 is a diagram illustrating coordinate axes set in the fluorescence image data by the region-of-concern defining section 339 in FIG. 26. FIG. 28 is a graph showing variations in pixel grayscale level along profiles P11 and P12 in FIG. 27.

The region-of-concern defining section 339 defines regions of concern CR11 and CR12 based on the rate of spatial change in pixel grayscale level in the input fluorescence image data.

As shown in FIG. 27, first, the region-of-concern defining section 339 sets X and Y axes in the fluorescence image data. The region-of-concern defining section 339 then extracts variations in pixel grayscale level along profiles substantially parallel to the X axis. FIG. 27 shows variations in pixel grayscale level along the profiles P11 and P12, which have certain Y-axis values (see FIG. 28). The profile P11 is a profile extending across the region of concern CR11, and the profile P12 is a profile extending across the region of concern CR12. In the graph of FIG. 28, coordinates on the X axis in FIG. 27 are plotted as "X" along the horizontal axis, and the grayscale values of the pixels are plotted as "Z" along the vertical axis.

Although the profile P11 is a profile related to the region of concern CR11, which is the region of the cancer MT, the grayscale levels of the pixels shown in FIG. 27 have lower values as a whole because the distance between the subject 3 and the distal end surface 27 of the insertion portion 5 is larger. On the other hand, although the profile P12 is a profile related to the region of concern CR12, which is the benign tumor BT, the grayscale levels of the pixels shown in FIG. 27 have higher values as a whole because the distance between the subject 3 and the distal end surface 27 is smaller.

Figure 29:
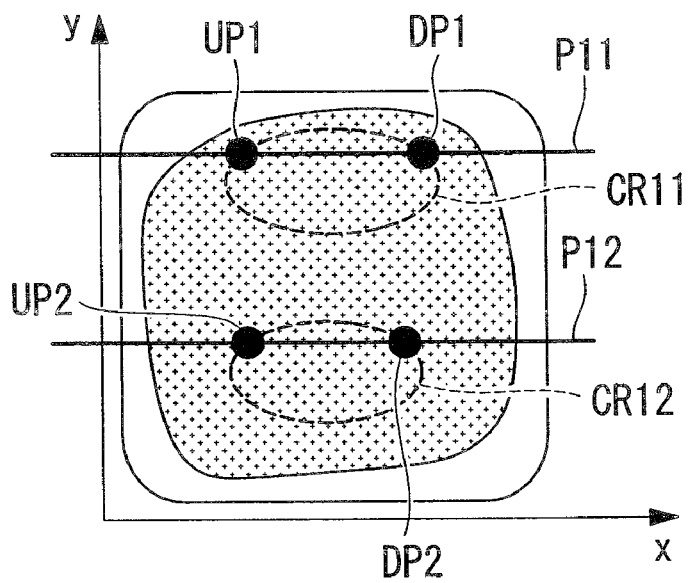
FIG. 29 is a diagram in which rising positions and falling positions are superimposed on the fluorescence image data.

FIG. 29 is a diagram in which rising positions UP1 and UP2 and falling positions DP1 and DP2 are superimposed on the fluorescence image data.

After acquiring the graph shown in FIG. 28, the region-of-concern defining section 339 extracts the rising positions UP1 and UP2 and the falling positions DP1 and DP2 in the variations in pixel grayscale level along the profiles P11 and P12. A rising position is a position including a sequence of a predetermined number or more of pixels (Pixel) satisfying the conditions $\delta Z/\delta X > 0$ and $|\delta Z/\delta X| >$ (predetermined value). A falling position is a position including a sequence of a predetermined number or more of pixels (Pixel) satisfying the conditions $\delta Z/\delta X < 0$ and $|\delta Z/\delta X| <$ (predetermined value).

The rising positions UP1 and UP2 and the falling positions DP1 and DP2 extracted by the region-of-concern defining section 339 are defined as the boundary positions of the regions of concern CR11 and CR12 and are superimposed on the fluorescence image data, as shown in FIG. 29.

The region-of-concern defining section 339 executes the above operation for profiles with all Y values at which the fluorescence image data is present to define the ranges of the regions of concern CR11 and CR12.

Subsequently, the region-of-concern defining section 339 defines representative pixels S1 and S2 in the regions of concern CR11 and CR12. The method for defining the representative pixels S1 and S2 and the methods for the subsequent operations executed by the image-generating unit 309 are similar to those of the first embodiment; therefore, a description thereof will be omitted.

In the above configuration, because the region-of-concern defining section 339 defines the regions of concern CR11 and CR12 based on the rate of spatial change in grayscale level related to fluorescence intensity, it can define regions that are possibly the cancer MT as the regions of concern CR11 and CR12.

The threshold used is not an absolute value of luminance but indicates whether the rate of spatial change therein continues for a predetermined amount, so that, even if there are pixels with high luminance occurring as local noise, no region of concern is defined there. Hence, regions of concern can be more accurately extracted.

The region-of-concern defining section 339 determines the rate of spatial change in grayscale level related to fluorescence intensity by determining the rate of change in grayscale level related to fluorescence intensity along, for example, the profiles P11 and P12 in the fluorescence image data. Because the grayscale level related to fluorescence intensity differs between the normal tissue N and the cancer MT, the boundary between the normal tissue N and the cancer MT has a high rate of change in grayscale level related to fluorescence intensity. Accordingly, the region-of-concern defining section 339 may define, as the regions of concern CR11 and CR12, regions whose grayscale levels related to fluorescence intensity are high by determining sites where the above rate of change is high.

Figure 30:
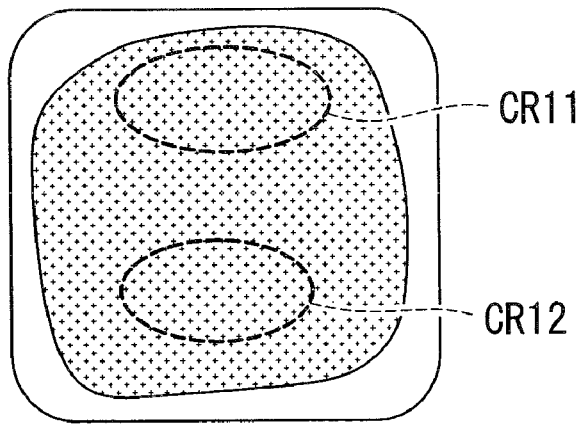
FIG. 30 is a diagram showing fluorescence image data subjected to a differentiation filter.

FIG. 30 is a diagram showing fluorescence image data subjected to a differentiation filter.

The region-of-concern defining section 339 may define the ranges of the regions of concern CR11 and CR12 by extracting a rising position and a falling position for each profile, as in the above embodiment, or may define the ranges of the regions of concern CR11 and CR12 by emphasizing the boundaries of the regions of concern CR11 and CR12 using a differentiation filter for determining the value of $|\delta^2 Z/\delta X \delta Y|$, as shown in FIG. 30; there is no particular limitation.

Figure 32:
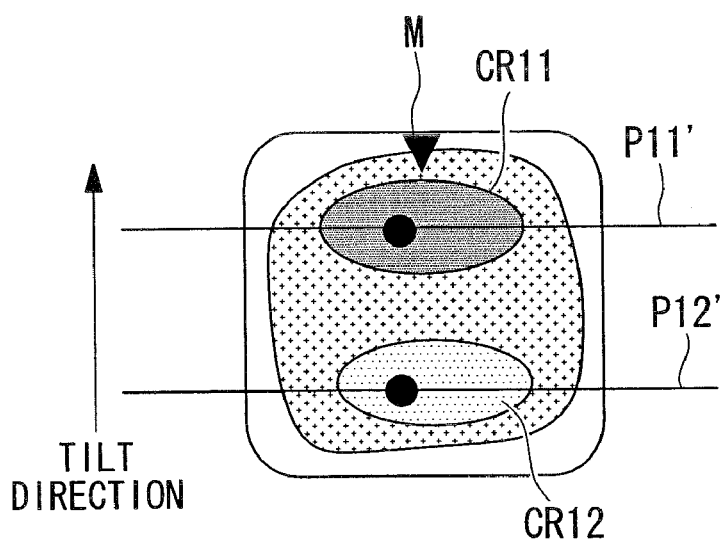
FIG. 32 is a schematic diagram illustrating the relative positional relationship between a subject and an insertion portion in FIG. 31.

FIG. 32 is a diagram illustrating another method of setting profiles with the fluorescence endoscope in FIG. 26. FIG. 32 is a schematic diagram illustrating the relative positional relationship between the subject and the insertion portion in FIG. 32.

Figure 31:
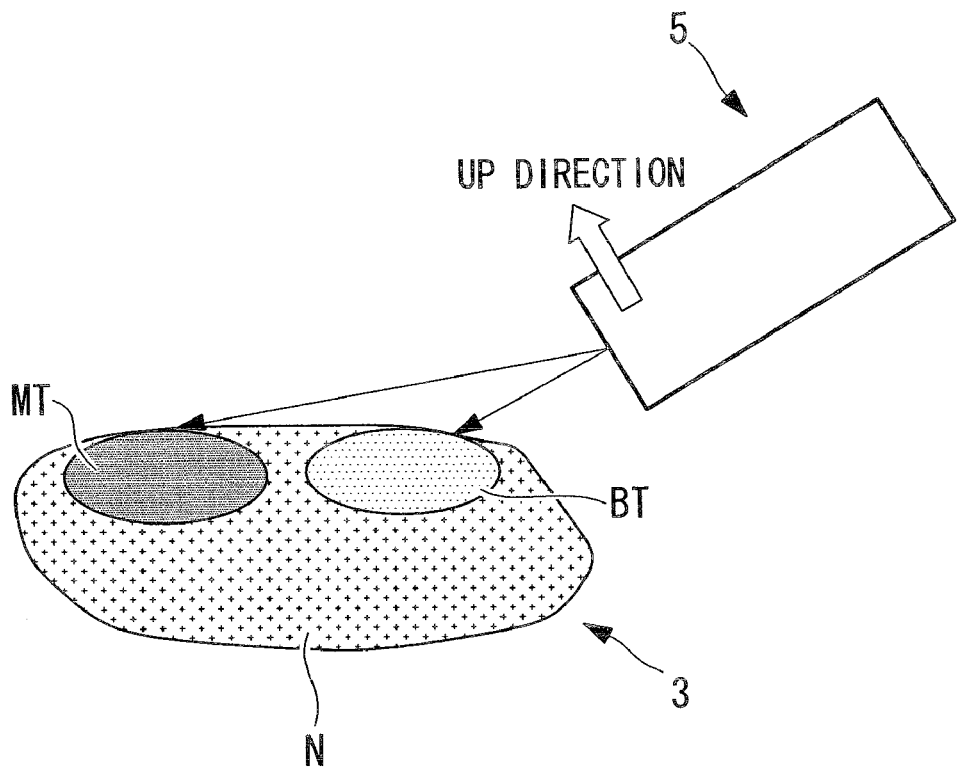
FIG. 31 is a diagram illustrating another method of setting profiles with the fluorescence endoscope in FIG. 26.

The region-of-concern defining section 339 may set profiles substantially parallel to the X axis, set in a predetermined direction, as in the above embodiment, or may set profiles P11' and P12' in a direction substantially perpendicular to the incident plane of excitation light and illumination light incident on the subject 3, as shown in FIG. 31; there is no particular limitation. The incident plane of the excitation light and so on is a plane orthogonal to the page in FIG. 32 and including the central axis line of the insertion portion 5.

The incident plane is also a plane including the tilt direction of the insertion portion 5. The tilt direction of the insertion portion 5 is the direction of the pitching movement of the distal end of the insertion portion 5. In the pitching movement, the UP direction of the insertion portion 5 is the direction in which a downward triangular mark M is located in FIG. 32 and is the arrow direction in FIG. 31. The operator determines the tilt direction of the insertion portion 5 from the position of the mark M in FIG. 32 and a reflected-light image. The profiles P11' and P12' are then set in a direction substantially perpendicular to the tilt direction of the insertion portion 5.

Because the profiles P11' and P12' are defined in a direction substantially perpendicular to the incident plane of the excitation light and so on, a predetermined distance related to neighboring regions can be defined while reducing the effect of the distance from the subject 3.

The distance from the illumination lens 15, from which the excitation light and so on incident on the subject 3 exit, to the surface of the subject 3 varies most in the direction along the incident plane. Accordingly, defining the predetermined distance related to the neighboring regions in the direction substantially perpendicular to the incident plane allows the distances from the endoscope end surface to the regions of concern to be substantially equal to the distances from the end surface of the endoscope to the corresponding neighboring regions, thus reducing the effect of the distance to the subject 3.

Third Embodiment

Next, a third embodiment of the present invention will be described with reference to FIGS. 33 to 35.

The basic configuration of a fluorescence endoscope of this embodiment is similar to that of the first embodiment but differs therefrom in the method for defining a region of concern and a neighboring region. In this embodiment, therefore, only the method, and the periphery thereof, for defining a region of concern and a neighboring region will be described using FIGS. 33 to 35, and a description of other components and so on will be omitted.

Figure 33:
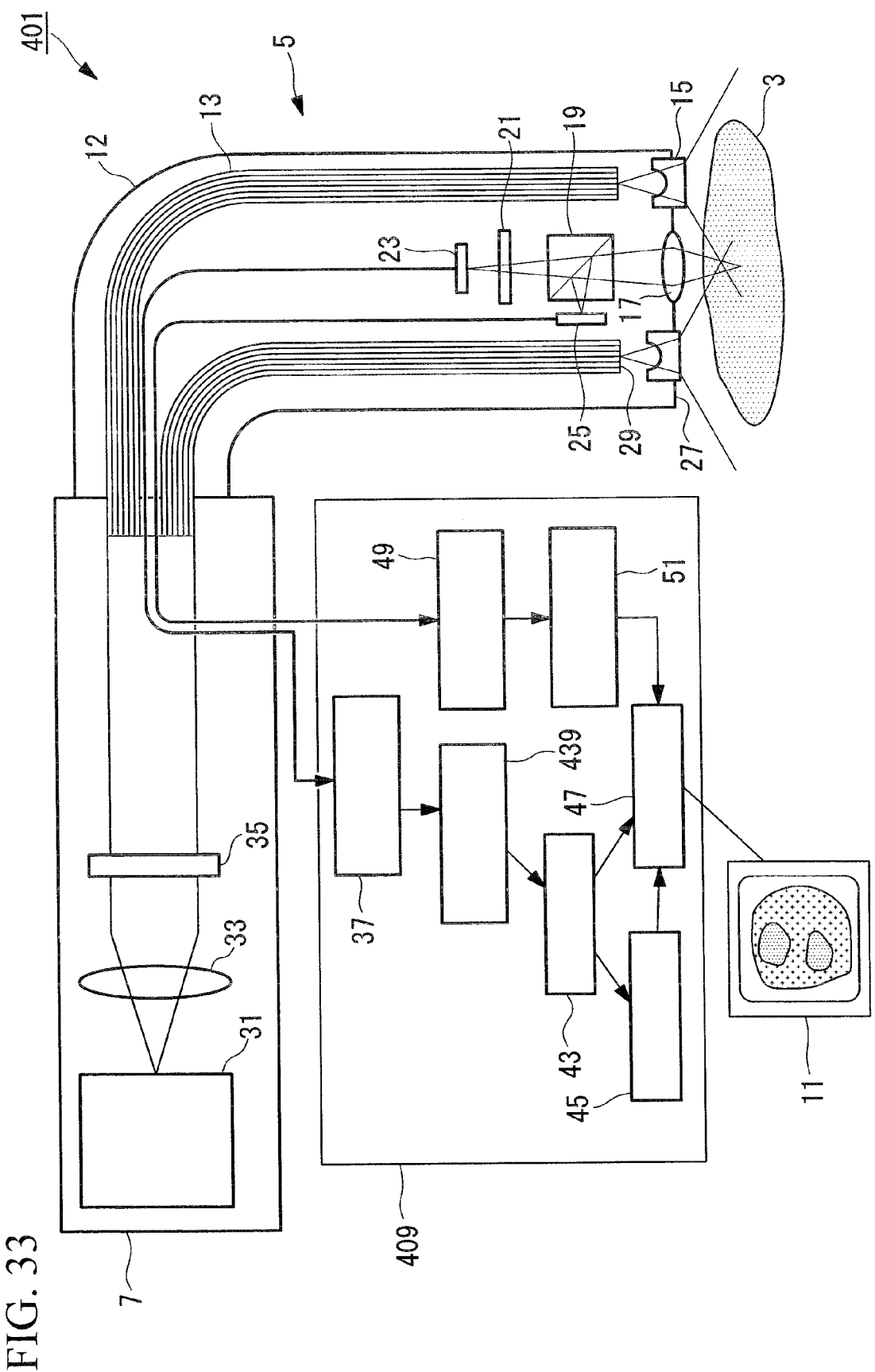
FIG. 33 is a schematic diagram illustrating the configuration of a fluorescence endoscope according to a third embodiment of the present invention.

FIG. 33 is a schematic diagram illustrating the configuration of the fluorescence endoscope according to this embodiment.

The same components as in the first embodiment are indicated by the same reference signs, and a description thereof will be omitted.

As shown in FIG. 33, a fluorescence endoscope 401 includes an insertion portion 5 for insertion into the body cavity of a subject 3, a light source unit 7, an image-generating unit 409, and a monitor 11.

The image-generating unit 409 includes a fluorescence-image generating section 37, a region-defining section (region-of-concern defining section, neighboring-region defining section) 439, an image-operation section 43, an image-identifying section 45, an image-combining section 47, a reflected-light-image generating section 49, and an examination-distance determining section 51.

The region-defining section 439 defines a region of concern and a neighboring region based on instructions input by the operator of the fluorescence endoscope 401. Fluorescence image data is input from the fluorescence-image generating section 37 to the region-defining section 439. Data related to the region of concern and the neighboring region and the fluorescence image data are output from the region-defining section 439 to the image-operation section 43.

Next, examination of the subject 3 and distinguishing between normal and affected areas with the fluorescence endoscope 401 having the above configuration will be described.

The case where the relative positional relationship between the subject 3 and the insertion portion 5 is the same as the positional relationship described in the first embodiment will be described herein.

The process in which the fluorescence endoscope 401 irradiates the subject 3 with excitation light and illumination light and inputs fluorescence image data for fluorescence contained in return light to the region-defining section 439 is similar to that of the first embodiment; therefore, a description thereof will be omitted.

Figure 34:
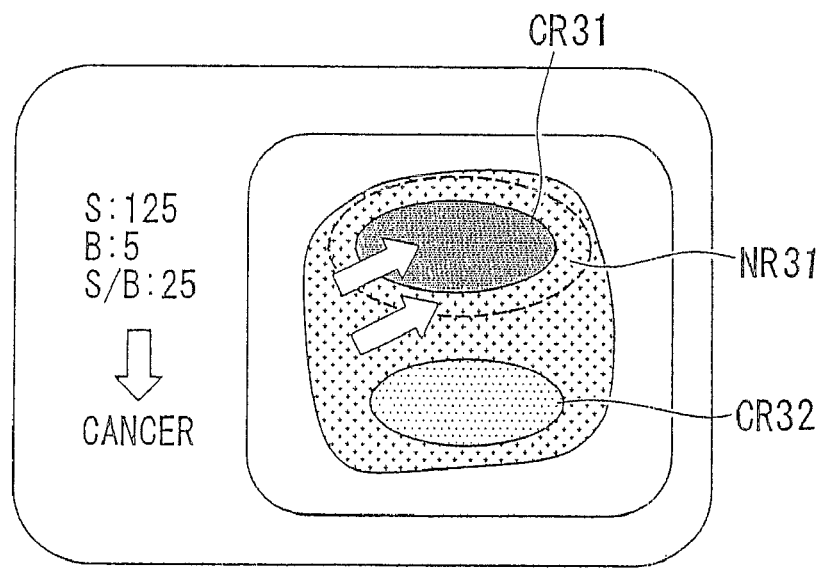
FIG. 34 is a schematic diagram showing a modification of selection of a region of concern and a neighboring region by a region-defining section in FIG. 33.

FIG. 34 is a schematic diagram showing an example of selection of a region of concern and a neighboring region by the region-defining section in FIG. 33.

When the fluorescence image data is input to the region-defining section 439, the fluorescence image data is displayed on the monitor 11 as a fluorescence image. The operator of the fluorescence endoscope 401 selects a region of concern and a neighboring region in the displayed fluorescence image while using a pointing device such as a mouse pointer. For example, as shown in FIG. 34, the operator selects a region of concern CR31 and an adjacent neighboring region NR31 in the fluorescence screen and inputs them to the region-defining section 439.

The region-defining section 439 outputs data related to the input region of concern CR31 and neighboring region NR31 and the fluorescence image data to the image-operation section 43. The methods for the subsequent operations executed by the image-generating unit 409 are similar to those of the first embodiment; therefore, a description thereof will be omitted.

Figure 35:
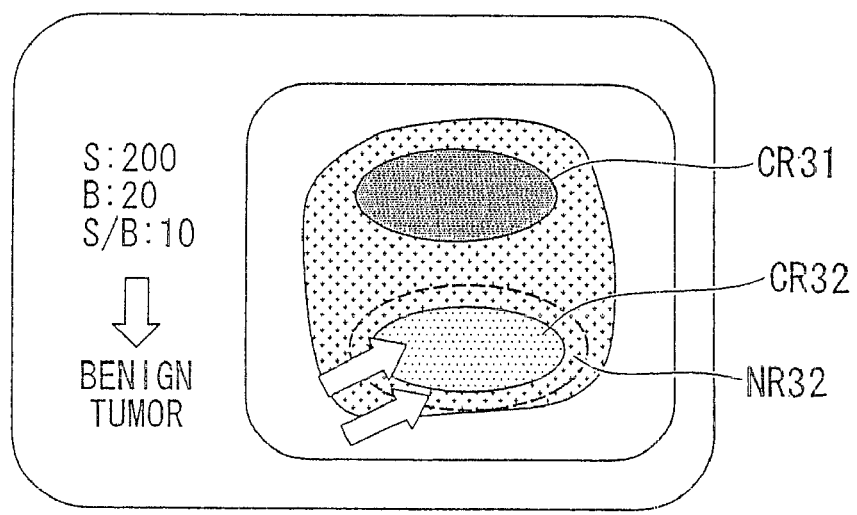
FIG. 35 is a schematic diagram showing another modification of selection of a region of concern and a neighboring region by the region-defining section in FIG. 33.

FIG. 35 is a schematic diagram showing another example of selection of a region of concern and a neighboring region by the region-defining section in FIG. 33.

On the other hand, as shown in FIG. 35, if the operator selects a region of concern CR32 and an adjacent neighboring region NR32 in the fluorescence screen and inputs them to the region-defining section 439, the region-defining section 439 outputs data related to the input region of concern CR32 and neighboring region NR32 and the fluorescence image data to the image-operation section 43. The methods for the subsequent operations executed by the image-generating unit 409 are similar to those of the first embodiment; therefore, a description thereof will be omitted.

By such a manual manipulation, a region of concern and a neighboring region can be reliably extracted even if the acquired image is extremely complicated and difficult to handle by automatic distinguishing.

The technical scope of the present invention is not limited to the above embodiments; various modifications are permitted without departing from the spirit of the present invention.

For example, the present invention can be applied to an embodiment in which the above embodiments are partially combined.

The invention claimed is:

1. A fluorescence endoscope comprising:
a light source that emits light for irradiation of a subject;
fluorescence image-acquiring section for acquiring an image of fluorescence contained in return light originating from the subject;
fluorescence-image generating section for generating fluorescence image data based on fluorescence-related data acquired by the fluorescence image-acquiring section;
region-of-concern defining section for defining a region of concern with a higher fluorescence intensity than a surrounding region based on the fluorescence image data;
neighboring-region defining section for defining a neighboring region near the region of concern on the basis of the same fluorescence image data as the fluorescence image data used for defining the region of concern; and
image-operation section for generating corrected image data based on a ratio of a grayscale level related to fluorescence intensity in the region of concern to a grayscale level related to fluorescence intensity in the neighboring region.

2. The fluorescence endoscope according to claim 1, wherein the region-of-concern defining section defines the region of concern based on a comparison between:
a grayscale level related to fluorescence intensity in the fluorescence image data; and
a predetermined threshold.

3. The fluorescence endoscope according to claim 1, wherein the region-of-concern defining section defines the region of concern based on a rate of spatial change in grayscale level related to fluorescence intensity in the fluorescence image data.

4. The fluorescence endoscope according to claim 1, wherein the neighboring-region defining section defines, as the neighboring region, a region up to a position separated by a predetermined number of pixels from a boundary of the region of concern.

5. The fluorescence endoscope according to claim 4, wherein the predetermined number of pixels is defined in a direction crossing an incident plane of the light incident on the subject.

6. The fluorescence endoscope according to claim 1, wherein the neighboring-region defining section defines, as the neighboring region, a region up to a position separated by a predetermined number of pixels from a predetermined position in the region of concern.

7. The fluorescence endoscope according to claim 1, wherein
the region-of-concern defining section includes region-of-concern representative-value calculating section for calculating a representative value of the grayscale level related to fluorescence intensity in the region of concern;

the neighboring-region defining section includes neighboring-region representative-value calculating section for calculating a representative value of the grayscale level related to fluorescence intensity in the neighboring region; and the image-operation section generates the corrected image data based on the ratio of the representative grayscale level of the region of concern to the representative grayscale level of the neighboring region.

8. The fluorescence endoscope according to claim 1, further comprising:

image-identifying section for identifying an affected area based on the corrected image data;

image-combining section for combining the corrected image data and the affected area identified by the image-identifying section to generate combined image data; and image-displaying section for displaying the combined image data.

9. The fluorescence endoscope according to claim 8, wherein the image-identifying section identifies the affected area based on a comparison between:

the ratio of the representative grayscale level of the region of concern to the representative grayscale level of the neighboring region; and a predetermined threshold.

10. The fluorescence endoscope according to claim 8, wherein the region-of-concern representative-value calculating section calculates the representative grayscale value of the region of concern based on a grayscale level related to the fluorescence intensity of fluorescence emitted from a fluorescent dye introduced into the subject; and the neighboring-region representative-value calculating section calculates the representative grayscale value of the neighboring region based on a grayscale level related to the intensity of autofluorescence emitted from the subject.

11. The fluorescence endoscope according to claim 1, further comprising:

reflected-light image-acquiring section for acquiring an image of reflected light contained in the return light;

reflected-light-image generating section for generating reflected-light image data based on reflected-light-related data acquired by the reflected-light image-acquiring section; and image-combining section for combining the reflected-light image data and the corrected image data.

12. The fluorescence endoscope according to claim 1, further comprising:

an insertion portion insertable into a body cavity of the subject; and light-conveying section for guiding the light emitted from the light source through the insertion portion to a distal end of the insertion portion and causing the light to exit toward the subject.

13. A fluorometry method comprising:

a fluorescence-image acquiring step of emitting light toward a subject and acquiring fluorescence image data related to fluorescence contained in return light from the subject;

a region-of-concern defining step of defining a region of concern with a higher fluorescence intensity than a surrounding region based on the fluorescence image data;

a neighboring-region defining step of defining a neighboring region near the region of concern based on the same fluorescence image data as the fluorescence image data used for defining the region of concern;

an operation step of generating corrected image data based on the ratio of a grayscale level related to fluorescence intensity in the region of concern to a grayscale level related to fluorescence intensity in the neighboring region; and an identification step of identifying an affected area based on the ratio of the grayscale level related to fluorescence intensity in the region of concern to the grayscale level related to fluorescence intensity in the neighboring region in the corrected image data and a predetermined threshold.

* * * * *